(12) United States Patent
Harks et al.

(10) Patent No.: US 11,096,659 B2
(45) Date of Patent: Aug. 24, 2021

(54) MONITORING APPARATUS FOR MONITORING AN ABLATION PROCEDURE

(71) Applicant: KONINKLIJKE PHILIPS N.V., Eindhoven (NL)

(72) Inventors: Erik A. Harks, Rijen (NL); Szabolcs Deladi, Veldhoven (NL); Jan F. Suijver, Dommelen (NL); Ladislav Jankovic, Fishkill, NY (US); Yan Shi, White Plains, NY (US); Wouter H. Rensen, Eindhoven (NL); Maya E. Barley, Watford (GB); Nijs C. Van Der Vaart, Rosmalen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 684 days.

(21) Appl. No.: 15/872,037

(22) Filed: Jan. 16, 2018

(65) Prior Publication Data
US 2018/0199911 A1 Jul. 19, 2018

Related U.S. Application Data

(62) Division of application No. 13/142,299, filed as application No. PCT/IB2010/050059 on Jan. 8, 2010, now Pat. No. 9,901,321.
(Continued)

(51) Int. Cl.
*A61B 8/08* (2006.01)
*A61B 8/12* (2006.01)
(Continued)

(52) U.S. Cl.
CPC .............. *A61B 8/0858* (2013.01); *A61B 8/12* (2013.01); *A61B 8/486* (2013.01);
(Continued)

(58) Field of Classification Search
CPC ......... A61B 8/0858; A61B 8/486; A61B 8/12; A61B 8/445; A61B 18/1495; A61B 18/02;
(Continued)

(56) References Cited

U.S. PATENT DOCUMENTS 5,196,006 A * 3/1993 Klopotek ............ A61F 9/00804
128/897
5,409,000 A 4/1995 Imran
(Continued)

FOREIGN PATENT DOCUMENTS

EP 0876796 A2 11/1998
WO 200051513 9/2000
(Continued)

OTHER PUBLICATIONS

Chiang et al., "IN-Vitro Ultrasound Temperature Monitoring in Bovine Liver During RF Ablation Therapy Using Autocorrelation", 2002 IEE Ultrasonics Symposium, pp. 1439-1442.
(Continued)

*Primary Examiner* — Peter Luong

(57) ABSTRACT

The present invention relates to a monitoring apparatus (101) for monitoring an ablation procedure. The monitoring apparatus (101) comprises an ultrasound signal providing unit for providing an ultrasound signal that depends on received echo series of an object (4) that is ablated. The monitoring apparatus (101) further comprises an ablation depth determination unit (103) for determining an ablation depth from the provided ultrasound signal. The ablation depth can be determined directly from the ultrasound signal and is an important parameter while performing an ablation procedure. For example, it can be used for determining the progress of ablation within the object (4) and for determining when the ablation has reached a desired progression.

15 Claims, 15 Drawing Sheets

Related U.S. Application Data

(60) Provisional application No. 61/144,494, filed on Jan. 14, 2009.

(51) Int. Cl.
*A61B 18/14* (2006.01)
*A61B 18/02* (2006.01)
*A61B 18/18* (2006.01)
*A61B 18/20* (2006.01)
*A61B 17/00* (2006.01)
*A61B 18/00* (2006.01)
*A61B 8/00* (2006.01)
*A61B 90/00* (2016.01)

(52) U.S. Cl.
CPC .......... *A61B 18/1492* (2013.01); *A61B 8/445* (2013.01); *A61B 18/02* (2013.01); *A61B 18/1442* (2013.01); *A61B 18/18* (2013.01); *A61B 18/20* (2013.01); *A61B 2017/00106* (2013.01); *A61B 2018/00577* (2013.01); *A61B 2018/00738* (2013.01); *A61B 2090/376* (2016.02); *A61B 2090/3784* (2016.02); *A61B 2218/002* (2013.01)

(58) Field of Classification Search
CPC ..... A61B 18/1442; A61B 18/18; A61B 18/20; A61B 2090/376; A61B 2090/3784; A61B 2017/00106; A61B 2018/00577; A61B 2018/00738; A61B 2218/002
See application file for complete search history.

(56) References Cited

U.S. PATENT DOCUMENTS

| | | |
|---|---|---|
| 6,746,401 B2 | 6/2004 | Panescu |
| 2002/0013529 A1 | 1/2002 | Smith et al. |
| 2003/0144653 A1* | 7/2003 | Francischelli ..... A61B 18/1492 606/32 |
| 2003/0208123 A1 | 11/2003 | Panescu |
| 2005/0283074 A1 | 12/2005 | Jackson et al. |
| 2006/0241445 A1* | 10/2006 | Altmann ................. A61B 8/12 600/443 |
| 2007/0073135 A1 | 3/2007 | Lee et al. |
| 2007/0083195 A1* | 4/2007 | Werneth ............. A61B 18/1492 606/41 |
| 2008/0045946 A1 | 2/2008 | Vaska |
| 2008/0097207 A1 | 4/2008 | Cai |
| 2008/0221448 A1 | 9/2008 | Khuri-Yakub et al. |

FOREIGN PATENT DOCUMENTS

| | | |
|---|---|---|
| WO | 2005122139 A2 | 12/2005 |
| WO | 2007026298 A2 | 3/2007 |
| WO | 2008065570 A1 | 6/2008 |

OTHER PUBLICATIONS

Dizaji et al., "Ultrasound Monitoring of Temperature Change in Liver Tissue During Laser Thermotherapy: 10C Intervals", Proceedings of the 29th Annual International Conference of the IEEE EMBS, Lyon, France, Aug. 23-26, 2007, pp. 2130-2133.

Varghese et al., "Ultrasound Monitoring of Temperature Change During Radiofrequency Ablation: Preliminary In-Vivo Results", Ultrasound in Medicine & Biology, vol. 28, Issue 3, Mar. 2002, pp. 321-329.

Yoon et al., Ultrasonic Phased Arrays with Variable Geometric Focusing for Hyperthermia Applications, Sch. of Electrical Engineering, Georgia Inst. of Technology, Atlanta, GA, vol. 39, Issue 2, Mar. 1992, 1 page.

* cited by examiner

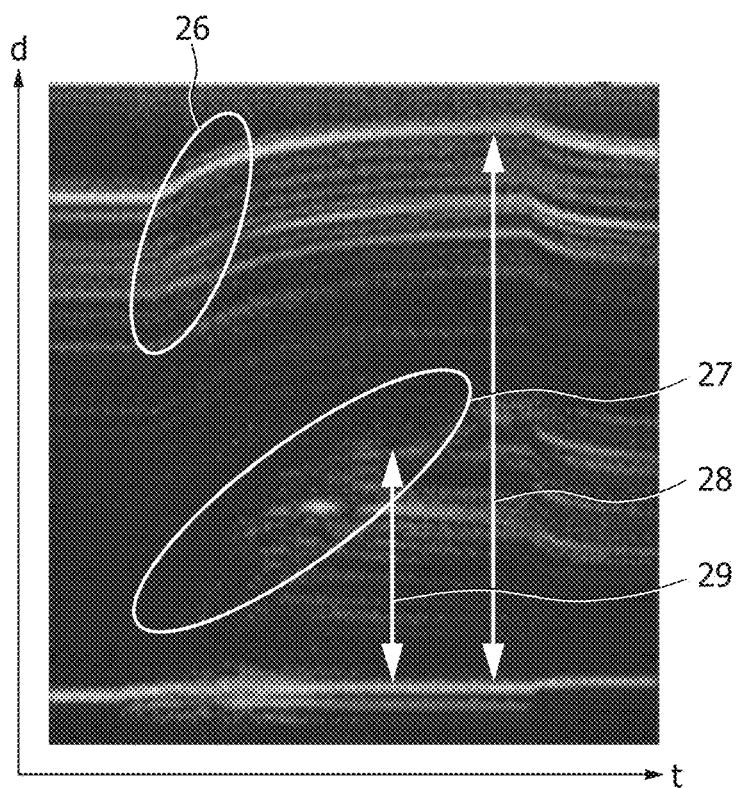
FIG. 3
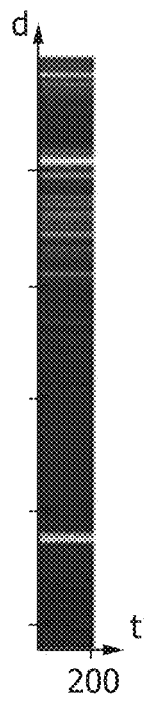 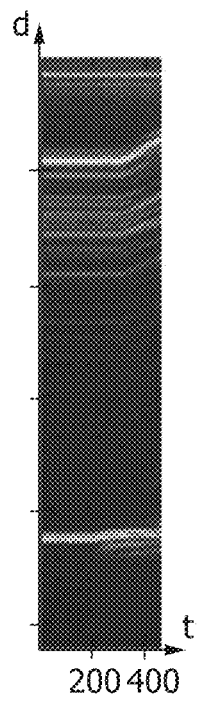 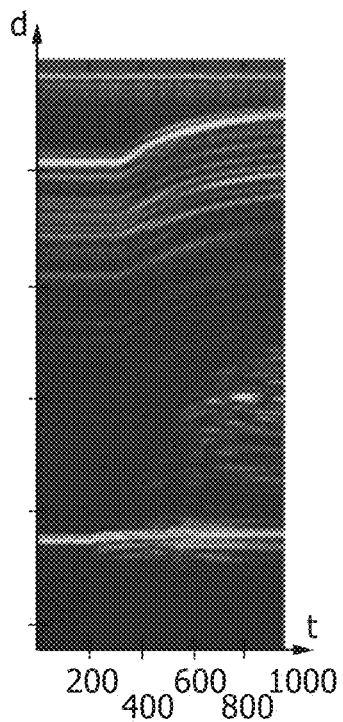
FIG. 4  FIG. 5  FIG. 6

MONITORING APPARATUS FOR MONITORING AN ABLATION PROCEDURE

REFERENCE TO RELATED APPLICATION

This is a divisional of prior application Ser. No. 13/142,299, filed Sep. 8, 2011.

FIELD OF THE INVENTION

The invention relates to a monitoring apparatus, a monitoring method and a monitoring computer program for monitoring an ablation procedure.

BACKGROUND OF THE INVENTION

The article "In-Vitro Ultrasound Temperature Monitoring in Bovine Liver during RF Ablation Therapy using Autocorrelation", Huihua Kenny Chiang et al., pages 1439 to 1442, IEEE Ultrasonic Symposium, 2002 discloses an apparatus for determining a two-dimensional temperature distribution in bovine liver tissue based on radio frequency (RF) ultrasound signals. The two-dimensional temperature map is used for thermal dosage control and real-time temperature monitoring during RF thermal therapy.

This apparatus has the drawback that an ablation therapy is not directly monitored, i.e. the apparatus does not provide direct information about the ablation status of the bovine liver tissue. Only the two-dimensional temperature map is determined, which only gives an indirect and inaccurate impression about the ablation status. A control of the ablation based on the two-dimensional temperature map is therefore also inaccurate.

SUMMARY OF THE INVENTION

It is an object of the present invention to provide a monitoring apparatus for monitoring an ablation procedure applied to an object more accurately. It is a further object of the invention to provide a corresponding monitoring method and a corresponding monitoring computer program.

In an aspect of the present invention a monitoring apparatus for monitoring an ablation procedure applied to an object is provided, wherein the apparatus comprises:

an ultrasound signal providing unit for providing an ultrasound signal produced by sending ultrasound pulses out to the object, receiving dynamic echo series after the ultrasound pulses have been reflected by the object, generating the ultrasound signal depending on the received dynamic echo series, an ablation depth determination unit for determining an ablation depth from the provided ultrasound signal.

Since the ablation depth determination unit determines the ablation depth from the generated ultrasound signal, it is not necessary to determine a two-dimensional temperature map which yields the above described inaccurate monitoring of the ablation procedure. In particular, the ablation depth can be determined directly from the generated ultrasound signal. Furthermore, the ablation depth is an important parameter while performing an ablation procedure. For example, it can be used for determining the progress of ablation within the object and for determining when the ablation depth has reached a predefined value, in particular, when a predefined degree of transmurality has been reached, if the object is a wall, in particular, a wall of a heart. The ablation depth can particularly be used for determining when cardiac tissue has become transmural. By determining the ablation depth from the ultrasound signal, an important parameter of ablation is accurately determined, thereby improving the accuracy of monitoring the ablation procedure.

If an ultrasound pulse is sent out to the object, the ultrasound pulse is reflected at different depths such that echo signals are received by the ultrasound unit at different times. The echo signals, which are generated by reflection of the ultrasound pulse at different depths within the object, form an echo series. By considering the speed of sound and the time, when an echo is recorded after the ultrasound pulse has been sent out into the object, the echo series can be translated into a dependence of an ultrasound reflection property of the object on the depth within the object.

Furthermore, several ultrasound pulses are sent out to the object at different times, thereby generating echo series at different times. These echo series, which are obtained from different ultrasound pulses at different times and, thus, which belong to different times, form dynamic echo series. The ultrasound signal which depends on the received dynamic echo series represents therefore the ultrasound reflection properties of the object at different depths and at different times.

By performing the ablation procedure preferentially a lesion is generated in the object. The ablation depth is preferentially defined by the boundary of the lesion within the object.

By determining the ablation depth at different times, the progression of ablation, in particular, the progression of the lesion boundary indicating the ablation depth can be determined.

The object is preferentially a heart wall, wherein the tissue of the heart wall is ablated.

The ultrasound signal providing unit can be any unit that provides the ultrasound signal. For example, the ultrasound signal providing unit can be a storing unit in which produced ultrasound signals are stored or it can be an ultrasound signal receiving unit for receiving a generated ultrasound signal as an input which can be used by the ablation depth determination unit for determining the ablation depth from the generated ultrasound signal.

It is preferred that the ablation depth determination unit is adapted to determine a discontinuity of the ultrasound signal and to determine the ablation depth as the depth of the ultrasound signal at which the discontinuity occurs. In particular, the provided ultrasound signal represents ultrasound reflection properties of the object at different depths and at different times, wherein the ablation depth determination unit is adapted to determine a discontinuity of the ultrasound signal and to determine the ablation depth as the depth of the ultrasound signal at which the discontinuity occurs.

A discontinuous variation can easily be distinguished from a continuous variation which generally relates to macroscopic tissue expansion. Thus, the determination of the ablation depth depending on discontinuities allows easily and accurately determining the ablation depth.

The ultrasound signal that depends on the received dynamic echo series can be represented as a two-dimensional image showing a reflection intensity depending on two-dimensions, for example, depending on the time on a horizontal axis and depending on the depth on a vertical axis. This two-dimensional image can also be regarded as a M-mode image. The ablation depth determination unit can be adapted to determine discontinuities in this two-dimensional image, wherein the ablation depth at a certain time is determined by determining the position in the two-dimensional image, at which the discontinuity has been determined. The ultrasound signal that depends on the received dynamic echo series can also be represented as a three- or four-dimensional image showing a reflection intensity depending on the time and two or three spatial dimensions, respectively. This allows determining the ablation depth in different directions in which ultrasound pulses have been sent out into the object.

It is further preferred that the provided ultrasound signal represents ultrasound reflection properties of the object at different depths and at different times, wherein the ablation depth determination unit is adapted to:
  correct the ultrasound signal for a thermal expansion of the object caused by the ablation procedure,
  determine the ablation depth and an ablation time as the depth and the time of temporally subsequent signal values of the corrected ultrasound signal, which correspond to the same depth and which are not similar with respect to a predefined similarity measure.

For correcting the ultrasound signal for a thermal expansion of the object caused by the ablation procedure the ablation depth determination unit can be adapted to estimate time-resolved shifts, in particular, macroscopic shifts, in the ultrasound signal due to tissue expansion. In particular, continuous variations of the ultrasound signal are detected and used for determining the shifts in the ultrasound signal due to tissue expansion for each time for which an ultrasound pulse has been sent out into the object and reflected by the object at different depths. Then, the ablation depth determination unit calculates a shift-compensated ultrasound signal to correct for the shift caused by tissue expansion during ablation.

The similarity measure can be determined by calibration measurements with an object having a known ablation depth. For example, by calibration a relative threshold can be defined indicating a maximum relative difference in signal values, in particular, in ultrasound signal intensities, leading to the decision that these signal values are regarded as being similar, i.e. a relative difference equal or below this maximum relative difference indicates that the corresponding signal values are similar.

It is further preferred that the provided ultrasound signal represents ultrasound reflection properties of the object at different depths and at different times, wherein the ablation depth determination unit is adapted to:
  correct the ultrasound signal for a thermal expansion of the object caused by the ablation procedure,
  determine stretches comprised of temporally subsequent signal values of the corrected ultrasound signal, which correspond to the same depth and which are similar with respect to a similarity measure,
  determine the ablation depth and an ablation time as the depth and the time at which the length of the stretches is below a predefined threshold.

This predefined threshold can be determined by a calibration measurement, wherein ultrasound signals are generated by sending ultrasound pulses into the object having a known ablation depth. In an embodiment, stretches having a length larger than 0.25 s, further preferred larger than 0.5 s and even further preferred larger than 1 s, are regarded as indicating that an ablation has not yet occurred at the respective depth.

It is further preferred that the ablation depth determination unit is adapted to apply a noise reduction filter on the ultrasound signal for reducing noise of the ultrasound signal. The noise reduction filter is preferentially a Hilbert filter. The noise reduction filter can also be another filter like a filter using a band pass, in particular a low-pass, cut-off frequency, or a filter using envelope detection. The noise reduction filter filters preferentially high frequencies out of the ultrasound signal, in particular, frequencies being larger than the half of the frequency of the ultrasound pulse. In an embodiment, frequencies larger 10 MHz are filtered out of the ultrasound signal. The noise reduction filter is preferentially adapted to allow reducing noise and other artifacts in the ultrasound signal. High frequency signal variations are filtered out by, for example, envelope detection. The high frequency components of the ultrasound signal are typically fluctuating due to small changes in temperature, alignment, power, composition of the object, in particular, of the cardiac tissue, et cetera.

It is further preferred that the provided ultrasound signal represents ultrasound reflection properties of the object at different depths and at different times, wherein the ablation depth determination unit is adapted to:
  correct the ultrasound signal for a thermal expansion of the object caused by the ablation procedure,
  determine, for different depth regions and at the different times, a cross correlation of temporally subsequent signal values of the same depth region,
  determine an ablation depth and an ablation time depending on the cross correlation of the temporally subsequent signals determined for the different depth regions and at the different times. In particular, the ablation depth determination unit is adapted to determine, for different depth regions and at the different times, a shift value depending on the determined cross correlation and to determine an ablation depth and an ablation time depending on the determined shift values, wherein a shift value is indicative of a shift between temporally subsequent signals within a depth region.

The ultrasound signal representing ultrasound reflection properties of the object at different depths and at different times is preferentially an M-mode image.

The cross correlation is preferably performed in the Fourier domain, i.e. preferentially before determining the cross correlation the ultrasound signal is Fourier transformed, and after the cross correlation has been determined and before the shift values are determined an inverse Fourier transformation is preferentially performed. This performing of the cross correlation in the Fourier domain results in faster processing.

Preferentially, the depth dimension is subdivided into different depth regions, wherein for each depth region each line of signal values defined by the same time is cross correlated with its temporally preceding line of signal values which belong to the same preceding time. Thus, for the respective depth region a number of cross correlation lines is determined. The cross correlation lines of the respective depth region are preferentially averaged. This averaging is preferentially performed by applying an average filter to the cross correlation lines of the respective depth region.

The shift value at a depth region and at a time is preferentially determined by determining a peak of the cross correlation line of the respective depth region at the respective time. The depth position of the respective peak within the respective depth region is indicative of the shift between the two lines of signal values within the depth region, which have been cross correlated for determining the cross correlation line. The shift value is therefore preferentially determined from the depth position of the peak within the respective depth region. The accuracy of determining the depth position of the peak within the respective depth region is preferentially improved by fitting a parabola to the peak, wherein the maximum of the parabola is used as the depth position of the peak within the depth region. Preferentially, the peak is cut out of the respective cross correlation line before performing the fitting procedure, in order to fit the parabola to the peak only and not to the respective complete cross correlation line within the respective depth region.

For determining the ablation depth and the ablation time a thresholding is preferably performed on the determined shift values. In an embodiment, if a shift value is larger than a predefined shift threshold, the corresponding depth region and time are preferentially regarded as ablation depth, at which the ablation process occurs, and as ablation time. A zone where tissue is coagulating corresponds to a region of poor cross correlation, i.e. corresponds to a region of a relatively large shift value. A healthy tissue zone and a zone including tissue that is already completely coagulated correspond to regions of good cross correlation, i.e. correspond to regions of a relatively small shift value. The zone at which tissue is actually coagulating can therefore be separated from a healthy tissue zone and a zone comprising tissue that is already completely coagulated by using the predefined shift threshold. This shift threshold can be predefined by, for example, calibration.

The determined shift values can be colored. For example, if the shift value indicates that the two subsequent lines of signal values, which have been used for determining the respective cross correlation line, are shifted with respect to each other in a first direction, the respective time and the respective depth region can be colored with a first color, and, if these two lines are shifted relative to each other in a second direction being opposite to the first direction, the respective time and depth region can be colored by a second color. In an embodiment, the first color is red and the second color is blue. The resulting colored image can be shown to a user, in particular, overlaid with the provided ultrasound signal being preferentially an M-mode image.

It is further preferred that the ultrasound signal providing unit comprises an ultrasound unit for
  sending ultrasound pulses out to the object,
  receiving dynamic echo series after the ultrasound pulses have been sent out to the object,
  generating an ultrasound signal depending on the received dynamic echo series. Thus, the ultrasound signal providing unit itself generates the ultrasound signal which is used for determining the ablation depth.

It is further preferred that the monitoring apparatus comprises an ablation unit for ablating the object. The ablation unit comprises preferentially energy application elements like electrodes for applying electrical energy, in particular, RF energy, or like optical elements for applying light energy, for example, optical fibers. The energy application element can also be a cryo-ablation element, a high intensity focused ultrasound element and/or a microwave element. The RF ablation electrodes are preferentially unipolar or bipolar. The ablation unit is preferentially arranged in a line or in a curve for ablating the object along a line or along a curve.

The monitoring apparatus preferentially further comprises an irrigation unit for irrigating a region of the object using, for example, a standard saline solution, in particular, for irrigating an ablated region of the object.

It is further preferred that the monitoring apparatus further comprises a control unit for controlling the ablation unit depending on the determined ablation depth. For example, the power and/or duration of applying ablation energy to the object can be controlled depending on the determined ablation depth. If the object is a wall and the thickness of the wall is known, for example, from a determination of the thickness by the ablation depth determination unit, the control unit is preferentially adapted to control the ablation unit depending on the thickness and the determined ablation depth. Preferentially, the control unit is adapted to ablate a heart wall until the resulting lesion is transmural.

The object is preferentially a heart wall, wherein it is further preferred that the monitoring apparatus is adapted to determine the thickness of the wall and repeatedly the ablation depth, wherein the ablation depth determination unit is adapted to determine repeatedly a degree of transmurality of ablation from the determined thickness and the determined ablation depth. In particular, the monitoring apparatus is adapted to terminate an ablation procedure, if a predetermined degree of transmurality of ablation has been reached. If the thickness of the wall is modified, for example, by the ablation procedure, preferentially also the determination of the thickness of the wall is also performed repeatedly.

It is further preferred that the object is a wall, wherein the ablation depth determination unit is adapted to determine the position of a front surface and a back surface of the wall from the ultrasound signal. In particular, the ablation depth determination unit is adapted to determine the thickness of the wall from the determined positions of the front surface and the back surface of the wall. Thus, the ultrasound signal can be used for determining the ablation depth and for determining the thickness of the wall, which is preferentially a wall of a heart, i.e. it is for example not necessary to provide a further unit for measuring the wall thickness. The thickness of the wall, the ablation depth and the degree of transmurality can be determined by using the ultrasound signal only.

Furthermore, since the ablation depth determination unit is adapted to determine the thickness of the wall from the ultrasound signal, an ablation procedure can be planned based on this determined thickness.

The monitoring apparatus preferentially further comprises a visualization unit for visualizing the ablation depth. In particular, the visualization unit is adapted for visualizing the progression of a lesion boundary. The visualization is preferentially performed in real-time.

It is further preferred that the ultrasound signal corresponds to an ultrasound signal that has been produced by directing ultrasound pulses periodically in different directions, for example, each ultrasound pulse can be regarded as an ultrasound beam, wherein the ultrasound beam is swept. Thus, echo series are received in different directions for producing a spatially two- or three-dimensional ultrasound signal. This spatially two- or three-dimensional ultrasound signal is produced several times at different times, thereby producing a time-dependent spatially two- or three-dimensional ultrasound signal depending on the received dynamic echo series. This allows scanning a larger region. The ablation depth determination unit is preferentially adapted to determine the ablation depth in one or several directions within a plane or volume covered by the time-dependent spatially two- or three-dimensional ultrasound signal.

For producing the spatially two- or three-dimensional ultrasound signal the ultrasound unit preferentially comprises a redirection element for redirecting the ultrasound pulses in different directions. The redirection element is, for example, a fluid lens, an electromechanical steering element, a mechanical rocker probe or another element for redirecting the ultrasound pulse. Furthermore, the redirection element can be integrated in a transducer of the ultrasound unit, for example, by using phased-array ultrasound transducers, or a capacitive micro-machined ultrasound transducer (CMUT) or a piezoelectric micro-machined ultrasound transducer (PMUT).

The ablation depth is preferentially determined in a direction in which an ultrasound pulse has been sent out.

It is further preferred that the monitoring apparatus comprises a catheter, wherein the ultrasound unit is located within the catheter.

This allows operating the monitoring apparatus within a hollow object like a heart. Furthermore, since the ultrasound can be arranged close to an inner surface of the object, high-frequency ultrasound can be used, if the object is living tissue, although high-frequency ultrasound has a small penetration depth only.

Preferentially also the ablation unit and/or the redirection element is located within or at the catheter. Furthermore, an irrigation element can also be arranged within the catheter.

The ultrasound unit is preferentially adapted to emit an ultrasound pulse having a frequency between 10 and 60 MHz, further preferred between 15 and 35 MHz.

The catheter preferentially comprises a catheter tip, wherein the catheter can be adapted to allow ultrasound pulses emitted by an ultrasound unit arranged within the catheter to leave the catheter straight from the tip and/or sideways. Preferentially, the catheter tip is adapted to provide an asymmetrical field of view such that the ultrasound pulses can be directed from a forward angle up to a sideways angle with respect to a direction along the catheter and pointing to the catheter tip. This field of view is preferentially achieved by a corresponding opening being, for example, a slot cut out of the catheter tip, wherein a redirection element is located within the opening.

The catheter is preferentially adapted such that the outside of the catheter is smooth; in particular, the catheter is preferentially adapted such that the outside of the catheter tip is smooth. For example, the catheter comprises an outside cover covering the catheter, in particular, the catheter tip, such that the outside surface of the catheter, in particular, of the catheter tip, is smooth.

It is further preferred that the catheter comprises a location sensor for determining the position and/or orientation of the catheter, in particular, of the catheter tip. If the ultrasound unit is located at a known position within the catheter, if the ablation depth is determined with respect to the position of the catheter and if the position and/or orientation of the catheter has been determined, the ablation depth with respect to a desired position and/or orientation of the catheter tip, i.e. of the ultrasound unit, can be determined.

It is further preferred that the monitoring apparatus comprises a sensing unit for sensing a property of the object. Also this sensing unit is preferentially arranged within the catheter. The sensing unit can comprise one or more mapping elements like electrodes for mapping the electrical activity of the object, which is preferentially a heart wall, or like another sensing element for sensing a property of the object like an optical element.

The monitoring apparatus preferentially comprises an ablation unit arranged in a line for ablating the object along a line, wherein the ultrasound unit is located adjacent to the line. In particular, the ablation unit is arranged in at least two lines, wherein the ultrasound unit is arranged between these at least two lines.

It is further preferred that the monitoring apparatus comprises an ablation unit arranged in a curve for ablating the object along a curve, wherein the ultrasound unit is located adjacent to the curve. In particular, the ablation unit is arranged in at least two curves, wherein the ultrasound unit is arranged between these at least two curves.

It is further preferred that the monitoring apparatus comprises an ablation unit located at a tip of a catheter, wherein the ultrasound unit is arranged around the ablation unit.

It is further preferred that the monitoring apparatus comprises an ablation unit located at a tip of a catheter and surrounding the ultrasound unit.

It is also preferred that the monitoring apparatus comprises a clamping unit including clamp jaws for clamping the object between the clamp jaws, wherein at least one of the clamp jaws comprises an ablation unit and wherein at least one of the clamp jaws comprises the ultrasound unit.

It is further preferred that the ablation depth determination unit is adapted to determine the ablation depth and/or position of the ablation region with respect to a determined wall surface, if the object is a wall, in particular, a heart wall.

In a further aspect of the present invention a monitoring method for monitoring an ablation procedure applied to an object is provided, the monitoring method comprising the steps of:
providing an ultrasound signal produced by
sending ultrasound pulses out to the object,
receiving dynamic echo series after the ultrasound pulses have been reflected by the object,
generating the ultrasound signal depending on the received dynamic echo series,
determining an ablation depth from the generated ultrasound signal.

In a further aspect of the present invention a monitoring computer program for monitoring an ablation procedure applied to an object is provided, the monitoring computer program comprising program code means for causing a monitoring apparatus as defined in claim 1 to carry out the steps of the monitoring method as defined in claim 13, when the computer program is run on a computer controlling the monitoring apparatus, It shall be understood that the monitoring apparatus of claim 1, the monitoring method of claim 13 and the monitoring computer program of claim 14 have similar and/or identical preferred embodiments as defined in the dependent claims.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated with reference to the embodiments described hereinafter. In the following drawings:

FIG. 3 shows schematically and exemplarily a two-dimensional representation of an ultrasound signal that depends on dynamic echo series, FIGS. 4 to 8 show schematically and exemplarily representations of different parts of an ultrasound signal that correspond to different time periods before, during and after an ablation procedure.

DETAILED DESCRIPTION OF EMBODIMENTS

Figure 1:
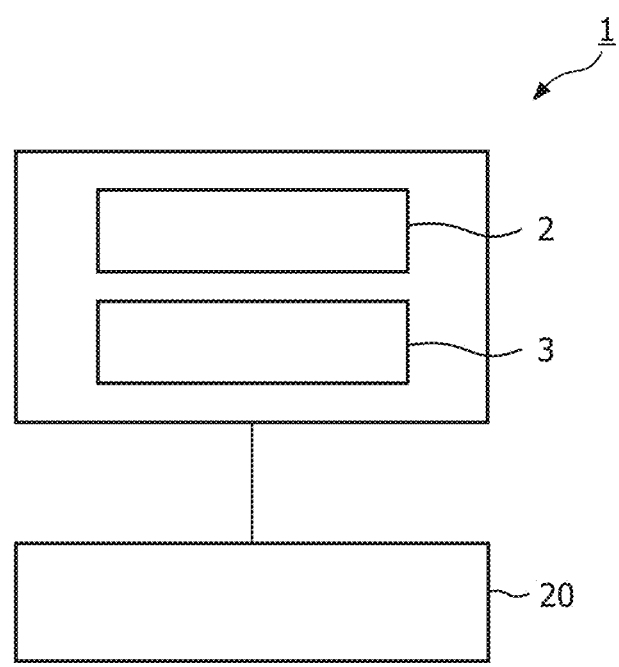
FIG. 1 shows schematically and exemplarily an embodiment of a monitoring apparatus for monitoring an ablation procedure applied to an object.

FIG. 1 shows schematically and exemplarily a monitoring apparatus 1 for monitoring an ablation procedure applied to an object. The monitoring apparatus 1 comprises an ultrasound signal providing unit 2 for providing an ultrasound signal produced by sending ultrasound pulses out to the object, receiving dynamic echo series after the ultrasound pulses have been reflected by the object and generating the ultrasound signal depending on the received dynamic echo series. The ultrasound signal providing unit 2 is, for example, a storing unit in which the ultrasound signals are stored for providing them, or the ultrasound signal providing unit is, for example, an ultrasound signal receiving unit for receiving ultrasound signals from an ultrasound unit and for providing these ultrasound signals. The ultrasound signal providing unit 2 can also be an ultrasound unit for producing the ultrasound signals as will be explained exemplarily further below.

The monitoring apparatus 1 further comprises an ablation depth determination unit 3 for determining an ablation depth from the provided ultrasound signal.

Figure 2:
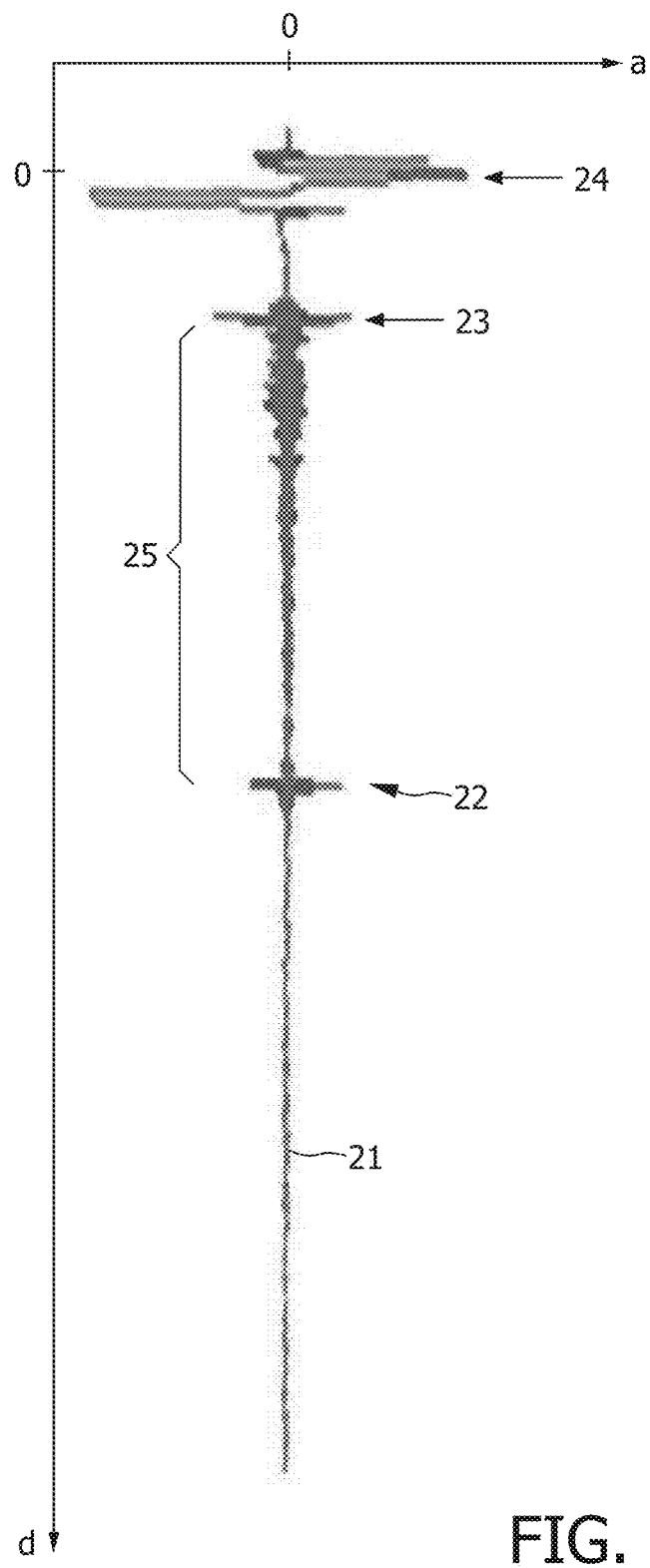
FIG. 2 shows schematically and exemplarily a representation of an echo series produced by reflections of an ultrasound pulse at heart wall tissue.

If an ultrasound pulse is sent out to the object, the ultrasound pulse is reflected at different depths such that echo signals are received by an ultrasound unit. The echo signals, which are generated by reflection of the ultrasound pulse at different depths within the object, form an echo series. An echo series 21 is schematically and exemplarily shown in FIG. 2. By considering the speed of sound and the time, at which an echo is recorded after the ultrasound pulse has been sent out to the object, the echo series can be translated into a dependence of an ultrasound reflection property of the object on the depths within the object. In FIG. 2, the amplitude a of the echo series in arbitrary units, which corresponds to the ultrasound reflection property, is shown depending on the depth d in arbitrary units that corresponds to the time, at which the respective echo has been received after the pulse has been sent out into the object.

In this embodiment, the object is a wall of a heart, wherein the ultrasound pulse is sent out into the heart tissue of the wall. In FIG. 2, the regions of the echo series 21 denote by 22 and 23, correspond to front and back surfaces of the heart wall. The region 24 is directly generated by the ultrasound pulse. Thus, in a strict sense, the echo series is the graph shown in FIG. 2 without region 24.

The echo series 21 shown in FIG. 2 allows determining the position of the front and back surfaces 22, 23 with respect to the position of an ultrasound unit that emits the ultrasound pulse and receives the echoes. The first measured amplitude in the region 24 marks the position of the ultrasound unit. Region 24 is followed by a region comprising an amplitude being substantially zero and after a while the amplitude increases again in region 23 marking the first reflection at the object, i.e. marking the front surface of the object. A region 25 comprising smaller amplitudes that correspond to reflections within the tissue of the heart wall follows, and then in the region 22 the amplitude increases again significantly thereby marking the back surface of the heart wall. Thus, the echo series 21 allows determining the positions of the front and back surfaces based on the regions 22 and 23. The region 25 in between is used for determining the ablation depth as will be explained further below.

The ablation depth determination unit is preferentially adapted to determine the position of the increasing amplitude in region 23 after a region comprising an amplitude value being substantially zero as the position of the front surface of the object. Then, the amplitude substantially decreases in region 25 and the position of the next significant increase of the amplitude (region 22) is determined as the position of the back surface of the heart wall. In other words, after the ring down of the transducer of the ultrasound unit in region 24 a "quiet period" ensues. This quiet period is subsequently terminated by a reflection in region 23 that is associated to the front surface. After this reflection in the region 23 a period 25 occurs that is marked by fast and small temperature changes in the ultrasound intensity. In particular, the envelope of the signal in the period 25 tends to have an exponential decrease in intensity. At the end of the period 25 again a strong reflection is observed in the region 22 that is associated to the back surface. Threshold values can predefined, in particular relative threshold values can be predefined, wherein the front surface is detected, if a reflection after the "quiet period" exceeds the respective predefined threshold and wherein the back surface is detected, if at the end of period 25 the signal exceeds the respective threshold. The thresholds can be predefined by calibration measurements with walls having known front surface and back surface positions.

The echo series 21 exemplarily shown in FIG. 2 has been generated by an ultrasound pulse that was sent out into the object at a certain time. Several of these ultrasound pulses are sent out to the object at different times, thereby generating echo series at different times. These echo series, which are obtained from different ultrasound pulses at different times, and, thus, which belong to different times, form dynamic echo series. The ultrasound signal which depends on the received dynamic echo series represents therefore the ultrasound reflection properties of the object at different depths and at different times. Such an ultrasound signal is schematically and exemplarily shown in FIG. 3.

In FIG. 3, different amplitudes of the ultrasound signal are indicated by different brightness, wherein a higher brightness corresponds to larger amplitude. The amplitude is shown depending on the depth d and the time t at which the respective echo series has been generated. The ultrasound signal shown in FIG. 3 forms an image that can be regarded as M-mode image.

By performing an ablation procedure, a lesion is generated in the heart wall, wherein the ablation depth is defined by the boundary of the lesion within the heart wall tissue.

The ablation depth determination unit is adapted to determine discontinuities in the ultrasound signal and to determine the ablation depth as a depth of the ultrasound signal at which the discontinuities occur. For example, in FIG. 3 in the first ellipse 26 only continuous variations of the ultrasound signal are present indicating a macroscopic tissue expansion of the heart wall tissue during applying ablation energy to the tissue. In the second ellipse 27 discontinuities in the variation of the ultrasound signal can be observed that indicate the ablation depth. Thus, FIG. 3 shows the progression of the lesion, i.e. the increasing ablation depth, in the second ellipse 27. Based on the observed discontinuities the ablation depth is determined as indicated exemplarily for a certain time by the second double arrow 29, whereas the first double arrow 28 indicates the thickness of the heart wall for a certain time. It should be noted that also the thickness of the heart wall changes with time during performing an ablation procedure due to a macroscopic tissue expansion as can be seen in FIG. 3.

For determining the ablation depth the ablation depth determination unit can be adapted to estimate time-resolved shifts, in particular, macroscopic shifts, in the ultrasound signal due to tissue expansion. In particular, the continuous variations of the ultrasound signal are detected and used for determining the shifts in the ultrasound signal due to tissue expansion for each time for which an ultrasound pulse has been sent out into the object and reflected by the object at different depths. Then, the ablation depth determination unit calculates a shift-compensated ultrasound signal to correct for the shift caused by tissue expansion during ablation. In particular, for different times the amplitude values shown in for example, FIG. 3 are moved vertically in correspondence with the determined shift for compensating this shift caused by tissue expansion. Then, preferentially the ablation depth determination unit suppresses noise in the shift-compensated ultrasound signal using, for example, a Gaussian filter with, for example, $\sigma=25$. In an embodiment, the ablation depth determination unit is adapted to follow lines corresponding to a constant depth in the shift-compensated ultrasound signal with time, i.e. to follow horizontal lines in a representation of the shift-compensated ultrasound signal that corresponds to the representation shown in FIG. 3, until a disjunctive event occurs. The length of the horizontal lines before this disjunctive event occurs is determined by means of correlation statistics. Then, the ablation depth determination unit is adapted to assign ablated/non-ablated regions based on the determined lengths of connected stretches with a cut-off parameter that remains flexible. The cut-off parameter is, for example, 0.25 s. In particular, in a shift-compensated ultrasound image temporally adjacent pixels on a horizontal line are compared. If along a horizontal line a lesion boundary is not present, the pixels along the horizontal line tend to have roughly the same intensity and only slow variations may occur. In contrast, if a lesion boundary, i.e. the ablation lesion, reaches the horizontal line, the intensity of the pixels in this line change significantly. The depth associated with this significant change in the intensity defines the ablation depth. Preferentially, the ablation depth determination unit is adapted to determine stretches along a horizontal line comprising pixel values having substantially the same intensity. When an ablation front reaches a certain horizontal line, a significant decrease in the length of the stretches in this horizontal line is observed. If the length of the stretches is below a predefined threshold, the ablation depth determination unit determines the ablation depth as the depth associated to the location at which the length of the stretches is below this predefined threshold. This predefined threshold can be determined by calibration measurements, wherein ultrasound signals are generated by sending ultrasound pulses into the object having a known ablation depth. Also the similarity measure for determining whether adjacent pixel intensity values on a horizontal line are similar or not, i.e. whether two adjacent pixel value intensities on a horizontal line belong to the same stretch, can be determined by this calibration. For example, by calibration a relative threshold can be defined indicating the maximum relative difference in the pixel value intensities leading to the decision that these pixel value intensity values are regarded as being similar, i.e. two pixel value intensities are regarded as being similar if their relative difference is equal to or smaller than the maximum relative difference that is preferentially determined by calibration. In an embodiment, stretches having a length larger than 0.25 s, further preferred larger than 0.5 s and even further preferred larger than 1 s, are regarded as indicating that the ablation has not yet occurred at the depth corresponding to the respective horizontal line.

In a further embodiment, the ablation depth determination unit is adapted to Fourier transform the shift-compensated ultrasound signal in which noise has been preferentially suppressed by using, for example, a Gaussian filter. The depth dimension is subdivided into different depth regions, wherein for each depth region each line of signal values defined by the same time is cross correlated with its temporally preceding line of signal values which belong to the same preceding time. Thus, for the respective depth region a number of cross correlation lines is determined. The subdivision of the depth dimension in different depth regions corresponds to a sub division in a vertical direction in the M-mode image shown, for example, in FIG. 3. For example, the vertical lines can be subdivided into about 1000 depth regions. The number of depth regions can be predefined or can be selected automatically or by a user, for example, depending on the thickness of tissue to be examined or the ultrasound frequency. Preferentially, for very thin arterial tissue having a sub-millimeter thickness the number of depth regions is smaller than 1000 and for very thick ventricular tissue having a thickness being larger than 20 mm the number of depth regions is larger than 1000.

The cross correlation lines of the respective depth region are averaged. This averaging is preferentially performed by applying an average filter to the cross correlation lines of the respective depth region. The average filter has, for example, a filter width of eleven lines. However, the average filter can also have a wider or narrower filter width. Moreover, in this embodiment, the ablation depth determination unit is adapted to apply an inverse Fourier transformation on the averaged cross correlation lines of the different depth regions and to determine peaks within the depth regions of the inversely Fourier transformed cross correlation lines. Thus, preferentially, for each depth region and for each time a peak of the cross correlation line is determined.

In this embodiment, the ablation depth determination unit is adapted to determine the depth position of the peak within the respective depth region by cutting the peak out of the respective cross correlation line and by fitting a parabola to the cut out peak. The maximum of the fitted parabola defines the depth position of the peak within the respective depth region at the respective time.

The ablation depth determination unit is further adapted to determine for each depth region and for each time a shift value from the depth position of the peak within the respective depth region at the respective time. Since the peak is a peak of a cross correlation line, the depth position of the peak within the respective depth region is indicative of the shift between the two lines of signal values within the depth region, which have been cross correlated for determining the respective cross correlation line. The ablation depth determination unit can be adapted to determine the depth position of the peak within the respective depth region as the shift value or the ablation depth determination unit can be adapted to perform further steps for determining a shift value depending on the respective depth position of the peak within the respective depth region. For example, predefined assignments between depth positions of the peak within a depth region and shift values can be stored in the ablation depth determination unit and used for determining a shift value depending on the determined depth position of the respective peak within the respective depth region. These assignments can be determined, for example, by calibration.

In this embodiment, the ablation depth determination unit is adapted to determine an ablation depth and an ablation time depending on the shift values which have been determined for different depth regions and at the different times. For determining the ablation depth and the ablation time a thresholding is preferentially performed on the determined shift values. If a shift value is larger than a predefined shift threshold, the corresponding depth region and time are regarded as an ablation depth, at which the ablation process occurs, and as ablation time, respectively. This shift threshold is predefined and stored in the ablation depth determination unit and can be determined by calibration measurements.

The ablation depth determination unit can be adapted to color the shift values. For example, if the shift value indicates that the two subsequent lines of signal values, which have been used for determining the respective cross correlation line, are shifted with respect to each other in a first direction, the respective time and the respective depth region can be colored with a first color, for example, a blue color, and, if these two lines are shifted relative to each other in a second direction being opposite to the first direction, the respective time and depth region can be colored by a second color, for example, a red color. The resulting colored image can be shown to a user on a visualization unit 20, in particular, overlaid with the provided ultrasound signal being preferentially an M-mode image. The first direction is, for example, a shift of a vertical line in FIG. 3 within a depth region in a down direction with respect to a preceding line and the second direction can be a corresponding up direction.

Preferentially, the ablation depth determination unit is adapted to apply a noise reduction filter being a high-frequency filter on the ultrasound signal. In this embodiment, the high-frequency filter is a Hilbert filter. In another embodiment, the high-frequency filter can also be another filter like a filter using a band pass cut-off frequency or a filter using envelope detection. FIG. 3 shows an ultrasound signal on which a Hilbert filter has been applied.

For interpreting the ultrasound signal shown in FIG. 3, the graph can be interrupted into various parts and re-plotted as exemplarily shown in FIGS. 4 to 8.

In FIGS. 3 to 9 the ultrasound signal for a constant time, i.e. the ultrasound signal along a vertical line in these figures, could be regarded as A-line of the ultrasound signal. In FIGS. 3 to 9 the ultrasound signal is shown depending on the depth d within the heart tissue wall and the time t in arbitrary units.

In FIG. 4, the ablation procedure is not applied, for example, a radio frequency ablation electrode is not operated. Thus, the ultrasound signal is constant with respect to variations in time, i.e. the reflection properties of the tissue of the heart wall are substantially not modified.

Figure 7:
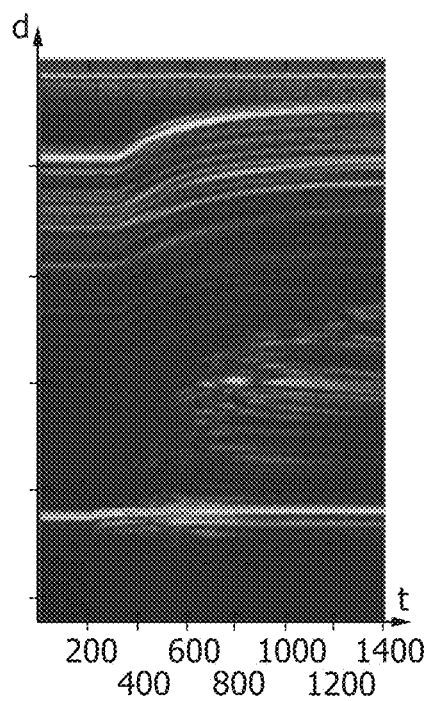
Figure 8:
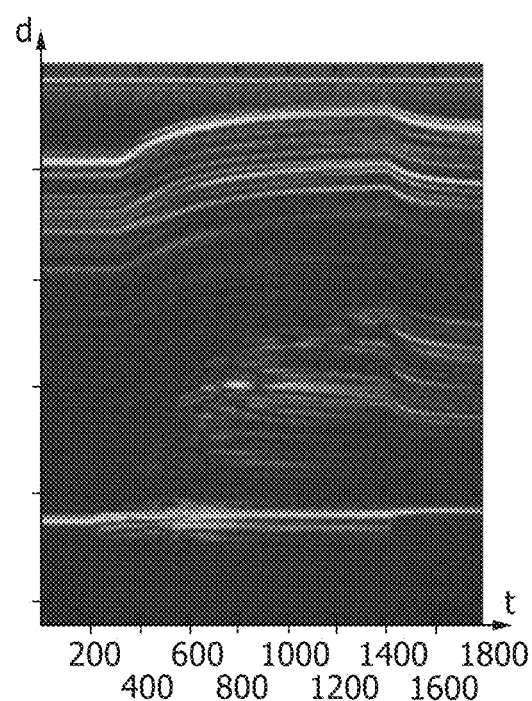

Upon ablation, the part of the tissue that is in contact with an ablation element, like an ablation electrode at a catheter tip, heats up and the ultrasound signal originating from that region starts to change (FIG. 5). It can also be observed that the heated region expands due to the thermal load and pushes the yet not heated part of the tissue in a direction that corresponds to a direction from the bottom to the top in FIGS. 3 to 8. In FIGS. 6 and 7 it is shown how the ultrasound signal changes if the ablation procedure continues. In FIG. 8, the ablation procedure has been stopped. i.e. the heat source (ablation element) has been switched off, resulting in shrinkage by cooling down and a shift of the stripes that correspond to the back surface of the heart tissue wall back towards the original position before ablation. The part of the tissue which was not treated and where no dynamical signal changes are observed preserves its thickness and just shifts its position.

Figure 9:
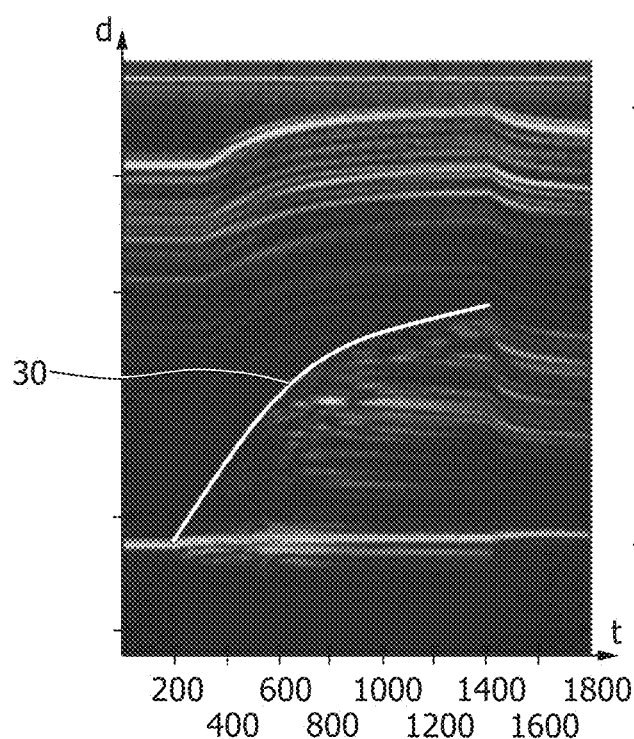
FIG. 9 shows exemplarily a determined ablation depth and a two-dimensional representation of the ultrasound signal.

FIG. 9 shows schematically and exemplarily a line 30 indicating the ablation depth determined by the ablation depth determination unit at different times, thereby indicating the progression of ablation. FIG. 9 further shows a slide bar 31 indicating the positions of the front surface and the back surface of the heart tissue wall by lines 32 and 34, respectively, and the ablation depth by line 33 for a certain time. In FIG. 9, the slide bar 31 is shown for the moment when the ablation stops. FIG. 9 can be shown on the visualization unit 20 for visualizing the progression in ablation.

Figure 10:
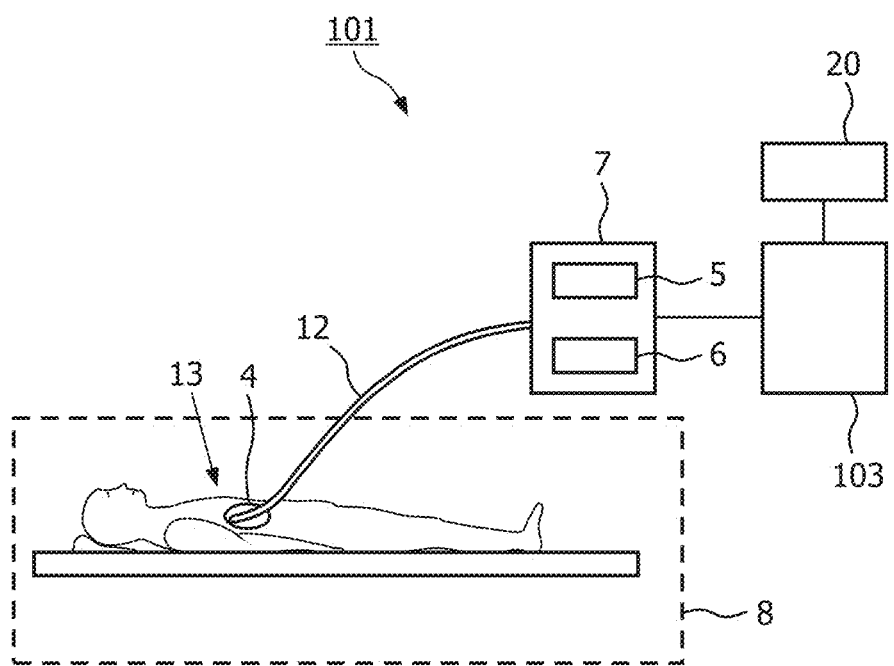
FIG. 10 shows schematically and exemplarily a further embodiment of a monitoring apparatus for monitoring an ablation procedure applied to an object.

FIG. 10 shows schematically and exemplarily another embodiment of a monitoring apparatus 101 for monitoring an ablation procedure applied to an object. The monitoring apparatus 101 comprises an ultrasound unit at a distal end of a catheter 12, i.e. at a catheter tip. The ultrasound unit (not shown in FIG. 10) is an ultrasound signal providing unit and controlled by an ultrasound control unit 5. The ultrasound unit and the ultrasound control unit 5 are adapted to send out ultrasound pulses to an object 4, to receive dynamic echo series after the ultrasound pulses have been reflected by the object and to generate the ultrasound signal depending on the received dynamic echo series. The object 4 is, in this embodiment, heart wall tissue of a patient 13 to which an ablation procedure is applied. In another embodiment, the ablation of another object like another organ of a person or of an animal or of a technical object can be monitored by the monitoring apparatus.

At the distal end of the catheter 12 an ablation unit for ablating the object 4 is located. The ablation unit (not show in FIG. 10) comprises energy application elements like electrodes for applying electrical energy, in particular, radio-frequency energy, or like optical elements for applying light energy, for example, optical fibers and/or other optical elements. The electrodes are preferentially unipolar or bipolar. The energy application elements are preferentially arranged in a line or in a curve for ablating the object along a line or along a curve.

The monitoring apparatus 101 further comprises a sub-control unit 6 for controlling the ablation element. The sub-control unit 6 and the ultrasound control unit 5 are integrated in a control unit 7. In other embodiments, the control units can be separate control units. Furthermore, the sub-control unit 6 is preferentially further adapted to control a steering of the catheter tip, a sensing of the heart wall tissue and/or an irrigation. In this case, the catheter comprises a steering element, a sensing element and/or an irrigation element, respectively. These different control functions can be performed by any other number of control units, for example, by a single control unit or by two or more than two control units.

The monitoring apparatus 101 further comprises an ablation depth determination unit 103 for determining an ablation depth from an ultrasound signal generated by the ultrasound unit. The ablation depth determination unit 103 is therefore adapted to receive an ultrasound signal from the ultrasound unit and to determine the ablation depth as described above with reference to the ablation depth determination unit 3, i.e. the ablation depth determination unit 3 and 103 are similar.

The sub-control unit 6 is adapted to control the ablation unit depending on the ablation depth determined by the ablation depth determination unit 103. For example, the power and/or duration of applying ablation energy to the object 4 are controlled depending on the determined ablation depth. The ablation depth determination unit 103 is adapted to determine the position of a front surface and a back surface of the heart wall 4 from the ultrasound signal and to determine the thickness of the heart wall depending on these positions, i.e. the corresponding depth positions are subtracted from each other to determine the thickness of the heart wall. The sub-control unit 6 is adapted to control the ablation unit depending on this determined thickness and the determined ablation depth. Preferentially, the sub-control unit 6 is adapted to ablate the heart wall tissue until a desired degree of transmurality of the heart wall tissue is reached, in particular, until the resulting lesion is transmural.

Preferentially, the monitoring apparatus 101 is adapted to determine the thickness of the heart wall 4 and the ablation depth repeatedly, wherein the ablation depth determination unit 103 is adapted to determine repeatedly a degree of transmurality of ablation from the determined thickness and the determined ablation depth. In particular, the monitoring apparatus 101 is adapted to terminate an ablation procedure, if a predetermined degree of transmurality of ablation has been reached.

Since the ablation depth determination unit 103 is adapted to determine the thickness of the wall 4 from the ultrasound signal, an ablation procedure can be planned based on this determined thickness.

The monitoring apparatus 101 further comprises a visualization unit 20 for visualizing the ablation depth. In particular, the visualization unit 20 is adapted for visualizing the progression of a lesion boundary. The visualization is preferentially performed in real-time. The visualization unit 20 is preferentially adapted to show the ultrasound signal, the progression of ablation, i.e. the lesion boundary, and the front and back surface positions as schematically and exemplarily shown in FIG. 9. The visualization unit 20 can also be adapted to show the ablation depth by just reporting the percentage of transmurality over time, i.e. in the case of FIG. 9 this would be about 50%.

Figure 11:
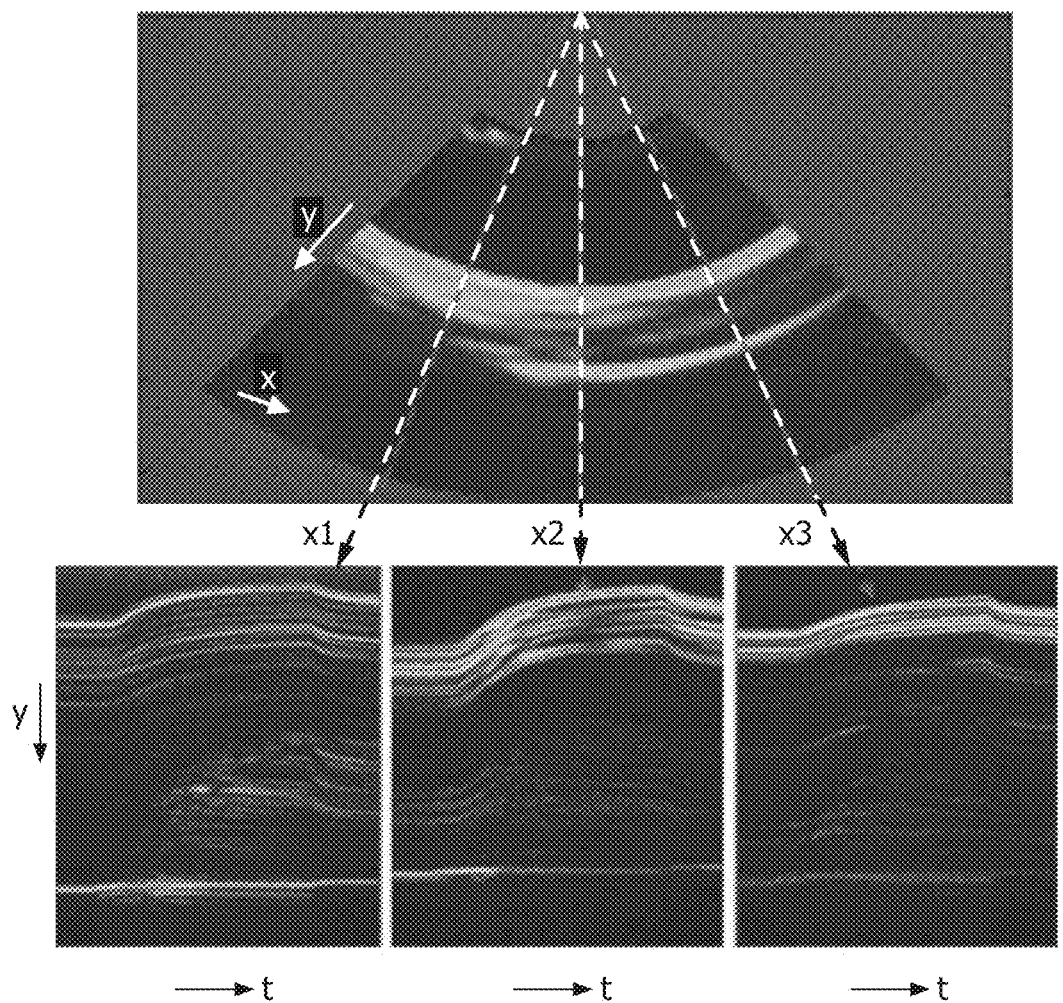
FIG. 11 shows exemplarily a spatially two-dimensional ultrasound signal.

The ultrasound unit can be adapted to direct ultrasound pulses in only one direction or periodically in different directions. For example, each ultrasound pulse can be regarded as an ultrasound beam, wherein the ultrasound beam is swept. Thus, echo series can be received in different directions for producing a spatially two- or three-dimensional ultrasound signal. A spatially two-dimensional ultrasound signal for a certain time is schematically and exemplarily shown in the upper part of FIG. 11. The arrows indicated by x and y are two spatial coordinates defining spatial positions in the spatially two-dimensional ultrasound signal. The broken arrows indicate ultrasound signals at the x positions, x1, x2 and x3, respectively. In the lower part of FIG. 11, the variation in time at these x positions before, during and after an ablation procedure is shown. The ablation depth determination unit 103 is preferentially adapted to determine the heart wall thickness and the ablation depth at different x positions, in particular, at these three x positions x1, x2 and x3. Thus, the spatially two- or three-dimensional ultrasound signal is produced several times at different times, thereby producing a time-dependent spatially two- or three-dimensional ultrasound signal depending on the received dynamic echo series. This time-dependent spatially two- or three-dimensional ultrasound signal is used for determining the thickness of the heart wall and the ablation depth in different directions. This allows scanning a larger region of the heart wall tissue.

For producing the spatially two- or three-dimensional ultrasound signal, the ultrasound unit preferentially comprises a redirection element for redirecting the ultrasound pulses in different directions. The redirection element is, for example, a fluid lens, an electromechanical steering element, a mechanical rocker probe or another element for redirecting the ultrasound pulses. Furthermore, the redirection element can be integrated in a transducer of the ultrasound unit, for example, by using phased-array ultrasound transducers like a capacitive micro-machined ultrasound transducer or piezoelectric micro-machined ultrasound transducer.

Figure 12:
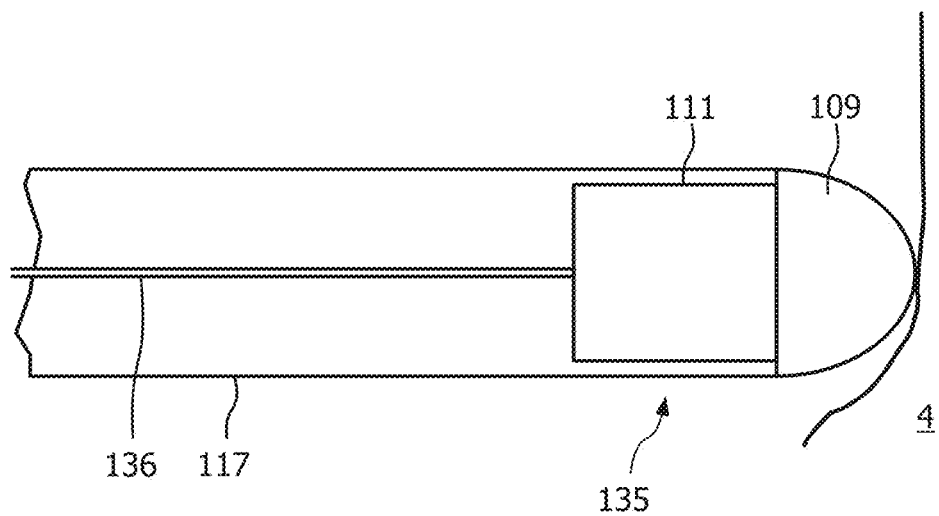
FIG. 12 shows schematically and exemplarily a catheter tip comprising an ultrasound unit and an ablation element.

FIG. 12 shows schematically and exemplarily an embodiment of a catheter tip 135 comprising an ultrasound device 111 within a tube of the catheter or a catheter shaft 117. The catheter tip 135 further comprises an ablation element 109 being a radio-frequency catheter electrode. A guiding element 136 is provided within the catheter for guiding signals from the control unit 7 to the ultrasound unit 111 and back from the ultrasound unit 111 to the control unit 7. The guiding element 136 is further adapted to guide electrical energy to the ablation element 109. The guiding element 136, which is only schematically shown in FIG. 12, is preferably comprised of several guiding elements for guiding signals and energy.

Preferentially, all ultrasound signals are continuously recorded with back-end data acquisition and an image construction instrument. Depending on the clinical needs different imaging devices/configurations can be employed. For a spatially one-dimensional imaging the ultrasound unit shown in FIG. 12 is preferentially a single element transducer with a frequency preferably falling between 10 MHz and 30 MHz In another embodiment, the ultrasound unit is preferentially adapted to emit an ultrasound pulse having a frequency between 10 and 60 MHz, further preferred between 15 and 35 MHz.

The ablation depth determination unit can be adapted to determine the ablation depth in different directions. The ablation depth determination unit can further be adapted to determine the direction in which the ablation has progressed furthest, i.e. in which the ablation depth is the deepest one.

A determination of the degree of transmurality can be based on the ablation depth in this determined direction. Furthermore, the ablation depth determination unit can be adapted to determine an ablation region, in particular, the shape and volume, based on the determined ablation depth in different directions. In an embodiment, also the ultrasound signal itself can be used to determine a lateral extension of the lesion. The ablation depth in different directions, the direction in which the ablation depth has progressed furthest, the determined ablation region and/or the determined lateral extension of the lesion can be stored and/or reported to a user like a clinician, for example, by using the visualization unit.

The determined ablation depth and thickness of the heart wall can not only be used to estimate a required ablation power and duration and/or to monitor the lesion formation, but can also be used to verify the lesion after ablation.

The catheter can be adapted to allow ultrasound pulses emitted by the ultrasound unit arranged within the catheter to leave the catheter straight from the tip and/or sideways. Preferentially, the catheter tip is adapted to provide an asymmetrical field of view such that the ultrasound pulses can be directed from a forward angle up to a sideways angle with respect to a direction along the catheter and pointing to the catheter tip. This field of view is preferentially achieved by a corresponding opening being, for example, a slot cut out of the catheter tip, wherein a redirection element is located within the opening for directing the ultrasound pulses within the asymmetrical field of view defined by the opening.

Figure 13:
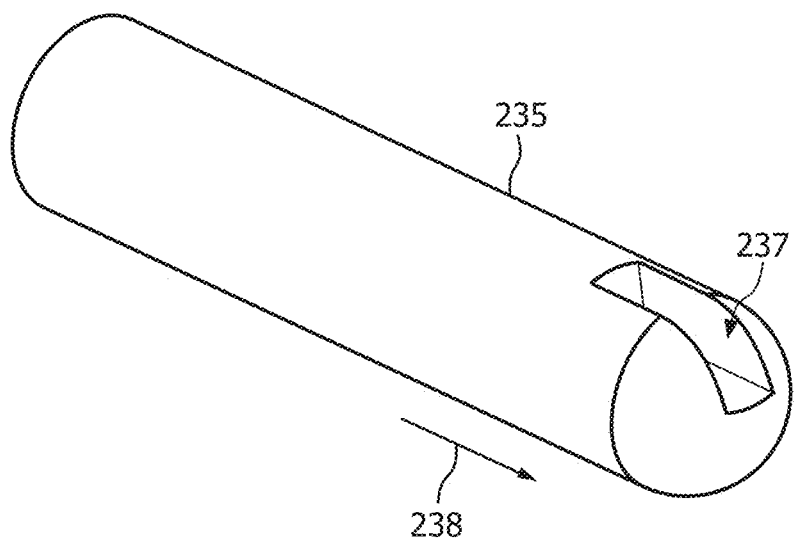
FIG. 13 shows schematically and exemplarily a catheter tip comprising a slot that is cut out of the catheter tip.

A catheter tip 235 with such an opening 237 providing an asymmetrical field of view such that the ultrasound pulses can be directed from a forward angle up to a sideways angle with respect to a direction 238 along the catheter and pointing to the catheter tip is schematically and exemplarily shown in FIG. 13.

The catheter is preferentially adapted such that at least the outside of the catheter tip is smooth; in particular, the catheter is preferentially adapted such that the outside of the complete catheter is smooth.

Figure 14:
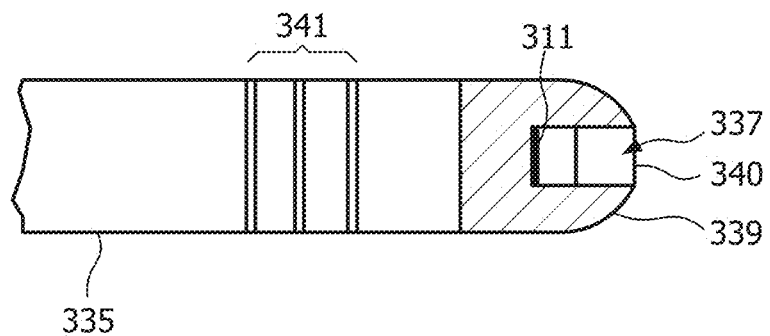
FIGS. 14 to 16 show a catheter tip comprising sensing electrodes, a sensing and ablation electrode and an ultrasound unit.
Figure 15:
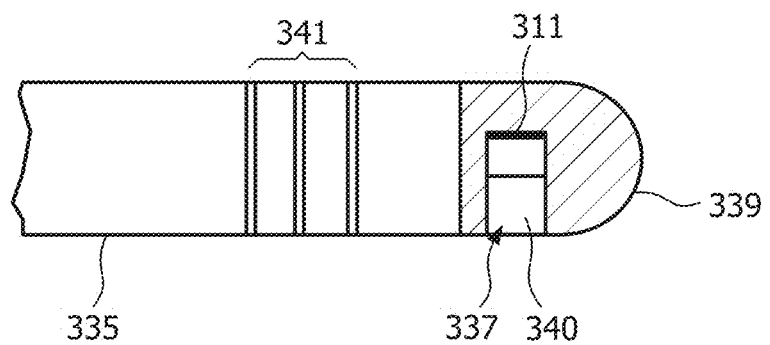
Figure 16:
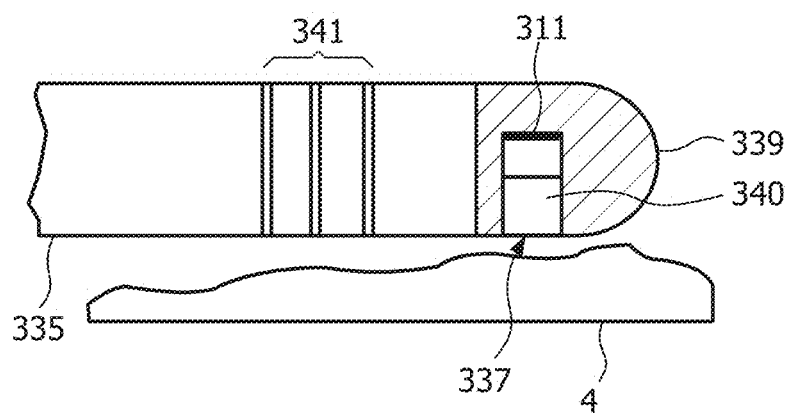

FIG. 14 shows schematically and exemplarily a further embodiment of a catheter tip 335. The catheter tip comprises sensing elements 341 being, in this embodiment, sensing electrodes for sensing the heart wall. The catheter tip 335 further comprises a sensing and ablation electrode 339 including an opening 337 in which an ultrasound unit 311 is located. In FIG. 14 the opening 337 is arranged such that ultrasound pulses can be emitted in a forward direction and in a side direction. FIG. 15 shows the same catheter tip, wherein the opening 337 is adapted to emit an ultrasound pulse in a side direction only. FIG. 16 shows the catheter tip 335 shortly before contacting the object 4, in particular, the tissue of the heart wall. A redirection element 340 is located within the opening 337 for directing ultrasound pulses in different directions. In a preferred embodiment, the redirection element 340 is a fluid lens that allows directing the ultrasound pulses in different directions as a function of time for generating spatially two- or three-dimensional ultrasound images. This allows determining the ablation depth in different directions. The fluid lens preferentially contains two immiscible fluids with different speeds of sound, wherein the arrangement of the two fluids within the fluid lens can be modified for changing the direction of the ultrasound pulse. This modification is, for example, caused by applying a voltage to the fluid lens which changes the arrangement of the two immiscible fluids by using the electrowetting effect.

The monitoring apparatus 101 is preferentially used in combination with a system for determining the position and/or orientation of the catheter, in particular, within the object 4, preferably, within a heart of a human being or an animal. In this embodiment, an imaging system like a magnetic resonance image system or an X-ray fluoroscopy system is used for determining the position and/or orientation of the catheter. This imaging system is indicated by the broken line 8 shown in FIG. 10. The catheter 12, in particular, the catheter tip can comprise elements for facilitating the determination of the orientation and/or position of the catheter by using the imaging system 8. For example, the catheter tip can comprise a tracking coil, if the catheter tip is used within a magnetic resonance imaging system, or elements that can be identified on an X-ray image and that are shaped such that a determination of the position and/or orientation of the catheter by using an X-ray fluoroscopy system is possible. The catheter tip can also comprise a location sensor for determining the position and/or orientation of the catheter, in particular, of the catheter tip within the object 4.

The positioning systems allows a user to position the catheter 12 within the heart, or more specifically, in the left atrium, of a patient. The user can position the catheter 12 in the correct position with respect to the heart wall to measure the wall thickness using the ultrasound signal generated by the ultrasound unit and the ablation depth determination unit. By using the determined position of the catheter tip, i.e. of the ultrasound unit, it is possible to display the thickness of the heart wall in an image of the heart. After collecting sufficient measurements, i.e. after determining the thickness of the heart wall at different locations on the heart wall, the user can then establish an ablation strategy including required power and duration depending on the determined heart wall thickness. It is also possible to use the catheter tip for tracing over the prior-performed ablation lesions for verification purposes. The continuity and depth of the lesions that have been created can be determined.

Figure 17:
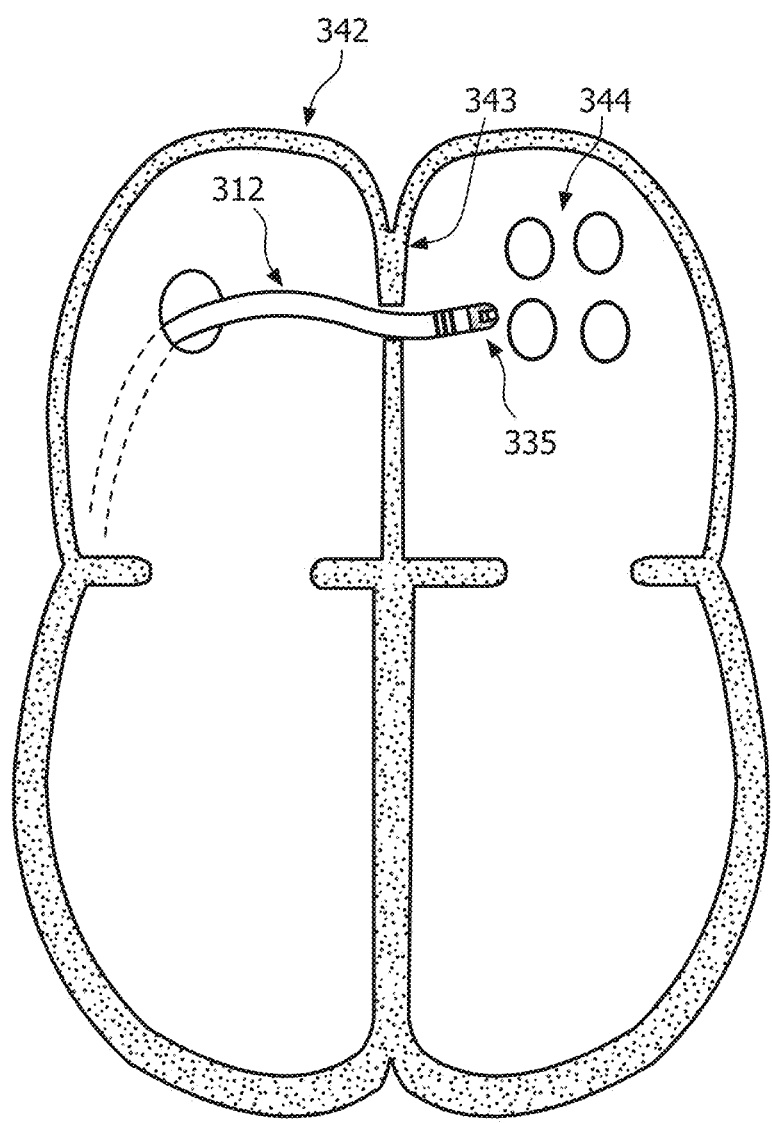
FIG. 17 shows schematically and exemplarily a catheter with a catheter tip located within a heart.

FIG. 17 shows schematically and exemplarily a heart 342 with atria and ventricles, in which a catheter 312 with the catheter tip 335 shown in FIGS. 14 to 16 has been introduced. The heart 342 comprises a septum 343 separating the right and left atrium and pulmonary vein openings 344 (four in total) in the left atrium.

The catheter can be used during the ablation of tissue of the heart wall. With the catheter, ultrasound scattering from the lesion is measured during the ablation, i.e. ultrasound signals are produced depending on dynamic echo series. Based on the ultrasound signal analysis performed by the ablation depth determination unit, the position and depth of the lesion with respect to the heart wall is established. In an embodiment, the position of the catheter tip is determined with respect to the position where the lesion has been created. This determination of the position can be performed by using a location sensor on the catheter tip combined with triangulation or by using another method, such as navigation based on imaging such as X-ray imaging or magnetic resonance imaging. Preferentially, the ultrasound unit in the catheter tip has a field of view which can be in the order of a view millimeters wide, thereby giving the positioning of the catheter some tolerance. The monitoring apparatus, in particular, the catheter, can be used to verify the lesion that is created during the ablation procedure.

Preferentially, the catheter tip that comprises the ultrasound unit is in contact with the object while the ultrasound unit sends ultrasound pulses out into the object. However, the monitoring apparatus can also be operated if the catheter tip is not in contact with the object.

Although preferentially the ultrasound unit and an ablation element are integrated in a catheter tip, i.e. although the ultrasound unit and the ablation element are preferentially located at the same side of the object, for example, the ultrasound unit and the ablation element are preferentially both located within a heart in front of a heart wall, in an embodiment the ablation unit and the ultrasound unit can be located at opposite sides of a wall being the object.

Figure 18:
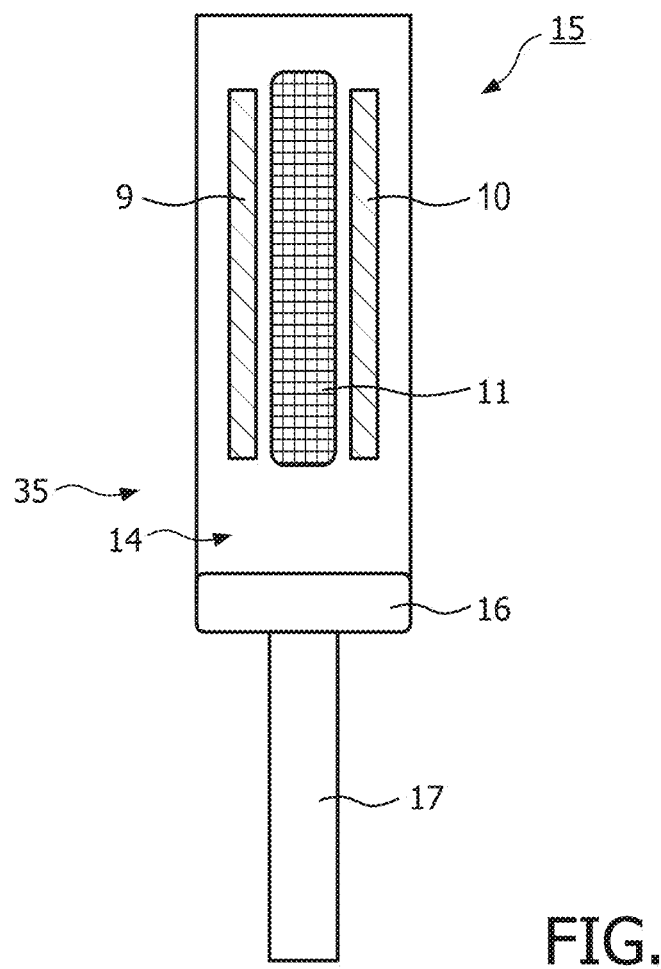
FIGS. 18 and 19 show schematically and exemplarily a linear ablation pen located at a distal end of a catheter.

FIG. 18 shows schematically and exemplarily a linear ablation pen located at the catheter tip 35 of a catheter comprising a catheter tube 17. The linear ablation pen 15 comprises a linear ultrasound unit 11 located between two linear ablation elements 9, 10 being, in this embodiment, ablation electrodes. The ultrasound unit 11 and the ablation elements 9, 10 are included in a backbone 14 of the ablation pen 15. The linear ablation pen 15 further comprises a pivot element 16 arranged at the end facing the tube 17 of the catheter for allowing pivoting the linear ablation pen with respect to the tube 17 of the catheter.

Figure 19:
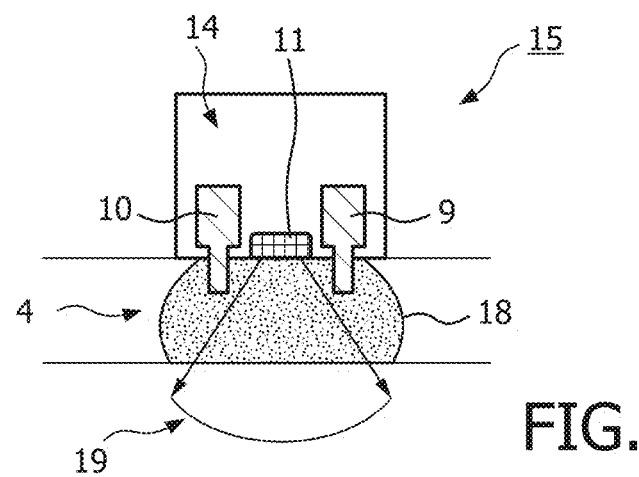

FIG. 19 shows another view of the linear ablation pen 15 arranged on the object being preferentially a heart wall. The two ablation electrodes 9, 10 have created a lesion 18, wherein this lesion 18, in particular the ablation depth of this lesion 18, is verified by the ultrasound unit 11 comprising the field of view 19.

The linear ablation pen 15 shown in FIGS. 18 and 19 can be used to "draw" lesion lines at an epicardial surface. Instead of two linear ablation electrodes 9, 10 only one or more than two ablation electrodes can be integrated into the catheter tip 15. Each of the ablation electrodes can be unipolar or bipolar. The ultrasound unit 11 can comprise a series of ultrasound transducers and/or a probe which allows a spatially two- and/or three-dimensional scanning, such as a phased array, a rocker probe, a fluid lens, a machined ultrasound transducer (MUT) array et cetera. If the probe allows spatially two-dimensional and/or three-dimensional scanning, the probe can be regarded as a combination of an ultrasound unit and a redirection element for redirecting the ultrasound pulses in different directions or the probe can be regarded as an ultrasound unit in which the redirection element is integrated as it is the case if, for example, a phased array is used. Preferentially, radiofrequency is used for ablating the heart tissue via the ablation electrodes 9, 10. However, another kind of energy like light energy can be used for ablation. For example, laser light, microwaves, cryogenic ablation, et cetera can be used for ablation. The linear ablation pen and also the other catheter tips described in this patent application can be constructed with or without an irrigation element to cool the tissue surface (not shown in FIGS. 18 and 19).

The monitoring apparatus, in particular, the catheter tip, in accordance with the invention can comprise a sensing element for sensing a property of the object. Also the sensing element is preferentially arranged within the catheter, in particular, within the catheter tip. The sensing element can comprise one or more mapping elements like electrodes for mapping the electrical activity of the object, which is preferentially a heart wall, or another sensing element for sensing a property of the object like an optical element.

Figure 20:
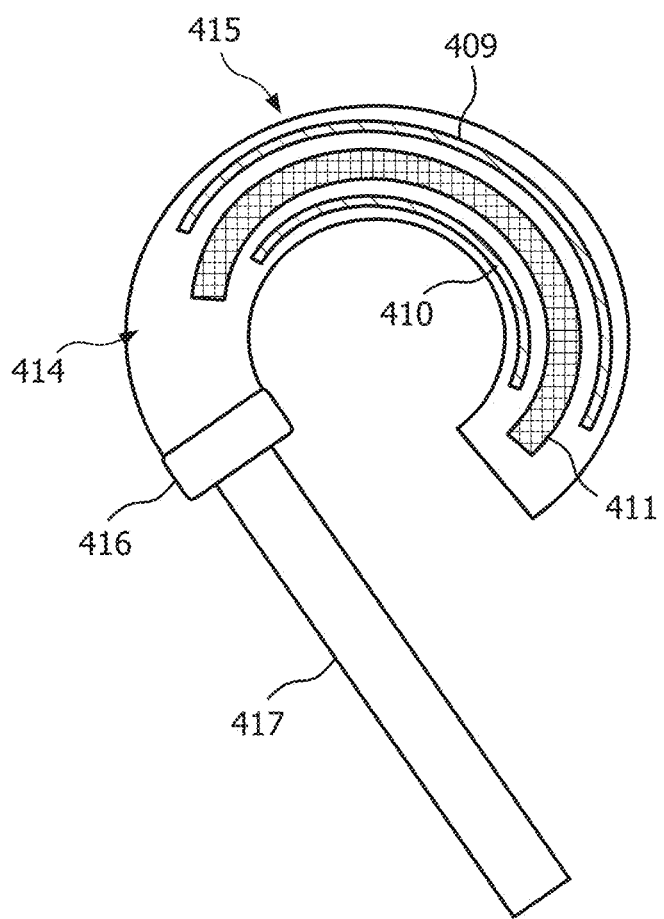
FIG. 20 shows schematically and exemplarily a lasso ablation catheter tip.

FIG. 20 shows schematically and exemplarily a catheter tip being a lasso ablation catheter tip 415 arranged on a distal end of a catheter tube 417. The lasso ablation catheter tip 415 is curved and comprises two curved ablation electrodes 409, 410, wherein a curved ultrasound unit 411 is arranged between the curved ablation electrodes 409, 410. The ablation electrodes 409, 410 and the ultrasound unit 411 are located in a backbone material 414 of the lasso ablation catheter tip 415. At the end of the lasso ablation catheter tip 415 facing the tube 417 of the catheter a pivot element 416 is arranged for pivoting the lasso ablation catheter tip 415 with respect to the tube 417.

The lasso ablation catheter tip 415 can be used to create a lesion around the pulmonary veins. The lasso ablation catheter tip 415 can comprise one or more than two ablation electrodes instead of the two ablation electrodes 409, 410. Each ablation electrode can be unipolar or bipolar. The ultrasound unit 411 can be a series of ultrasound transducers, or a probe which allows spatially two-dimensional and/or three-dimensional scanning, such as a phased array, a rocker probe, a fluid lens, a MUT array et cetera, as explained above with reference to FIGS. 18 and 19. Also the lasso ablation catheter tip 415 can be operated with radiofrequency energy for ablation, but alternatively other energies, in particular, other energy sources, like lasers, microwave sources et cetera can be used for ablation. Also the lasso ablation catheter tip can be constructed with or without irrigation to cool the tissue surface.

Figure 21:
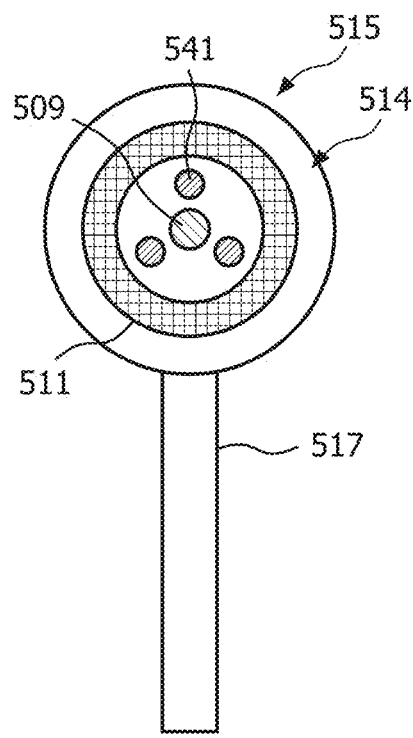
FIGS. 21 and 22 show exemplarily and schematically focal ablation pens located at a distal end of catheter.

FIG. 21 shows schematically and exemplarily a focal ablation pen 515 located at a catheter tip, in particular, located at the distal end of the tube 517 of a catheter. The focal ablation pen 515 comprises a circular ultrasound unit 511 surrounding three electrodes 541 for pacing or sensing, which are arranged at the corners of a triangle and which surround an ablation electrode 509. In this embodiment, the circular ultrasound unit 511 is centered with respect to the ablation electrode 509. The focal ablation pen 515 further comprises a backbone material 514 holding the ablation electrode 509, the electrodes 541 for pacing or sensing and the ultrasound unit 511.

Figure 22:
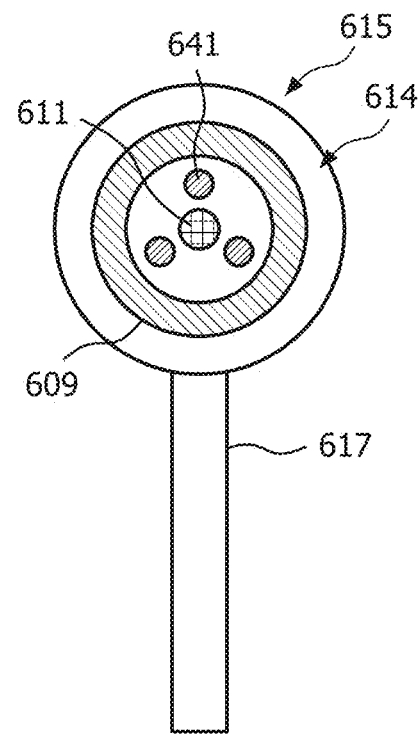

FIG. 22 shows schematically and exemplarily another embodiment of a focal ablation pen. The focal ablation pen 615 comprises a circular ablation electrode 609 surrounding three electrodes 641 for pacing or sensing that are located at corners of a triangle and that surround an ultrasound unit 611. The circular ablation electrode 609 is focus-centered with respect to the ultrasound unit 611. Also the focal ablation element 615 comprises backbone material 614 and is arranged at the distal end of a tube 617 of a catheter.

The focal ablation pens can be used for the focal ablation of proarrhythmogenic tissue spots, including ganglionic plexi. The focal ablation pen is not limited to a certain number of ultrasound units, ablation electrodes and/or electrodes for pacing and sensing. Each ablation electrode is a unipolar or bipolar electrode. The ultrasound unit can be a series of ultrasound transducers, or a probe which allows spatially two-dimensional and/or three-dimensional scanning, such as a phased array, a rocker probe, a fluid lens, a MUT array, et cetera, as describes above, for example, with reference to FIGS. 18 and 19. Also with the focal ablation pen preferentially a radiofrequency energy source is used for ablation. But, also other energy sources like lasers, microwave sources et cetera can be used for ablation.

If lasers are used as energy sources, of course, instead of ablation electrodes optical elements like ablation fibers or optical elements for directing light to the object are used.

Also the focal ablation pen can be constructed with or without an irrigation unit to cool the tissue surface.

Although the embodiments shown in FIGS. 21 and 22 comprise electrodes 541, 641 for pacing and sensing of electrical signals, in another embodiment, these electrodes can be omitted. Furthermore, an electrode for high-frequency pacing can be included to target ganglionic plexi.

Figure 23:
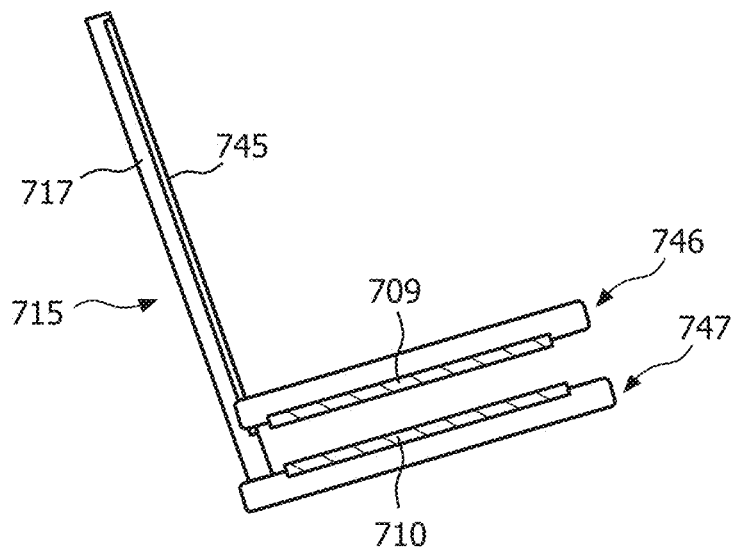
FIG. 23 shows schematically and exemplarily a bipolar clamp located at a distal end of a catheter.

FIG. 23 shows schematically and exemplarily a bipolar clamp 715 being preferentially located at a distal end of a catheter, i.e. the bipolar clamp 715 forms preferentially the tip of a catheter. The bipolar clamp 715 comprises a first jaw 746 and a second jaw 747 being adapted to clamp tissue between the first and second jaws 746, 747. In this embodiment, the second jaw 747 is fixed to the tube 717 of the catheter and the first jaw 746 is attached to a distal end of a rod 745 slidably arranged within the tube 717 of the catheter. Thus, by sliding the rod 745 towards the distal end of the catheter, tissue can be clamped between the first and second jaws 746, 747. Both jaws 746, 747 comprise an ablation electrode 709, 710.

Figure 24:
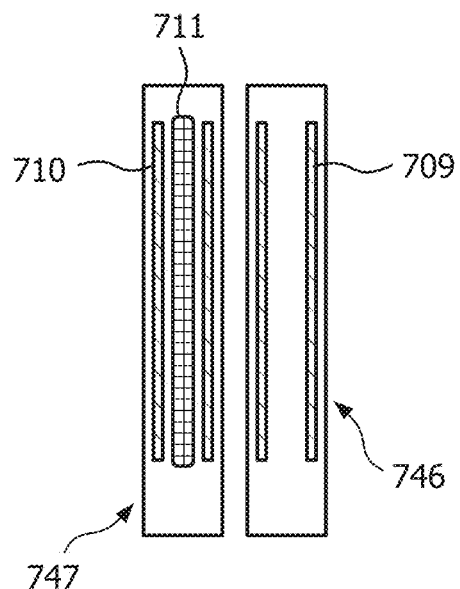
FIG. 24 shows schematically and exemplarily two jaws of the bipolar clamp.

FIG. 24 shows schematically and exemplarily the sides of the first and second jaws 746, 747 that face each other, if the two jaws clamp tissue. The first jaw 746 comprises two linear ablation electrodes 709 that are arranged parallel to each other. The second jaw 747 comprises two linear ablation electrodes 710 that are arranged parallel to each other, wherein a linear ultrasound unit 711 is arranged between the two linear ablation electrodes 710.

Figure 25:
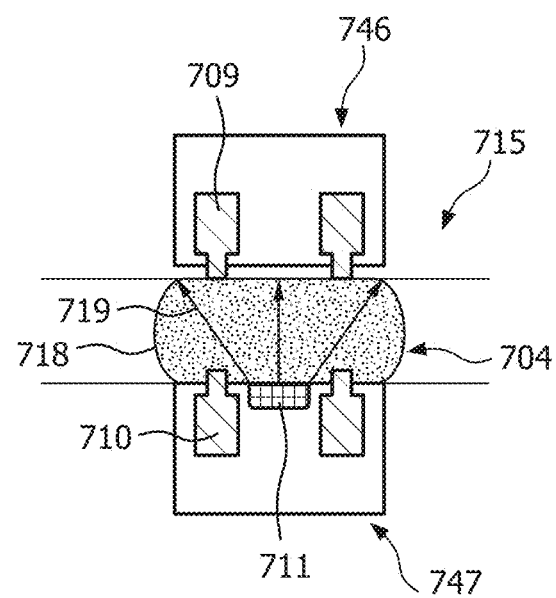
FIG. 25 shows the two jaws of the bipolar clamp clamping tissue.

FIG. 25 shows schematically and exemplarily the first jaw 746 and the second jaw 747 clamping tissue 704. A lesion 718 has been created within the tissue 704 by using the ablation electrodes 709, 710 and the ultrasound unit 711 verifies the lesion, in particular, generates ultrasound signals for determining the ablation depth. The arrows 719 indicate the field of view of the ultrasound unit 711.

The bipolar clamp 715 as shown in FIGS. 23 to 25 can be used to create a lesion by clamping tissue between the jaws 746, 747.

In another embodiment, a jaw can comprise only one or more than two ablation electrodes. Furthermore, each jaw can comprise at least one ultrasound unit. The ultrasound unit is preferentially located within the second jaw 747 being the lower jaw in FIG. 23. The ultrasound unit can be a series of ultrasound transducers, or a probe which allows spatially two-dimensional and/or three-dimensional scanning, such a phased array, a rocker probe, a fluid lens, a MUT array et cetera, as explained above with reference to FIGS. 18 and 19. Also with the bipolar clamp 715 a radio-frequency energy source is preferred for ablation. But, also other energy sources can additionally or alternatively be used for ablation, for example, lasers, a microwave source et cetera. If a laser is used as an energy source, of course, instead of ablation electrodes optical ablation elements are used, for example, optical fibers or another optical element for directing light to the tissue clamped between the two jaws. The surface of the jaws 746, 747 is preferentially atraumatic to prevent acute tissue damage. Thus, the surface of the jaws is preferentially smooth. The jaws are preferentially made of stainless steel. The jaws are preferentially tapered, wherein the cross section of the jaws increases from the ends facing the tube 717 towards the ends of the jaws pointing away from this tube to facilitate clamp placement and preferentially to not impede visualization. Furthermore, preferentially the clamped zone of tissue is wider than the zone of ablated tissue, in particular, significant wider. This allows squeezing out blood in the clamped zone out of the ablation zone, thereby reducing the likelihood of thrombus formation.

Figure 26:
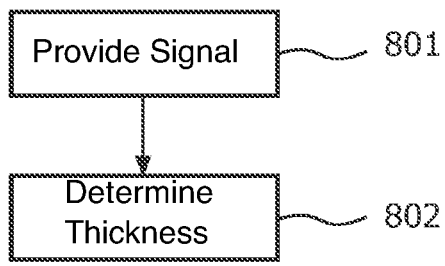
FIG. 26 shows exemplarily a flowchart illustrating an embodiment of a monitoring method for monitoring an ablation procedure applied to an object.

In the following an embodiment of a monitoring method for monitoring an ablation procedure applied to an object will be exemplarily described with respect to a flowchart shown in FIG. 26.

In step 801, an ultrasound signal is provided that is produced by sending ultrasound pulses out to the object, by receiving dynamic echo series after the ultrasound pulses have been reflected by the object and by generating the ultrasound signal depending on the received dynamic echo series.

In step 802, an ablation depth is determined from the generated ultrasound signal.

Figure 27:
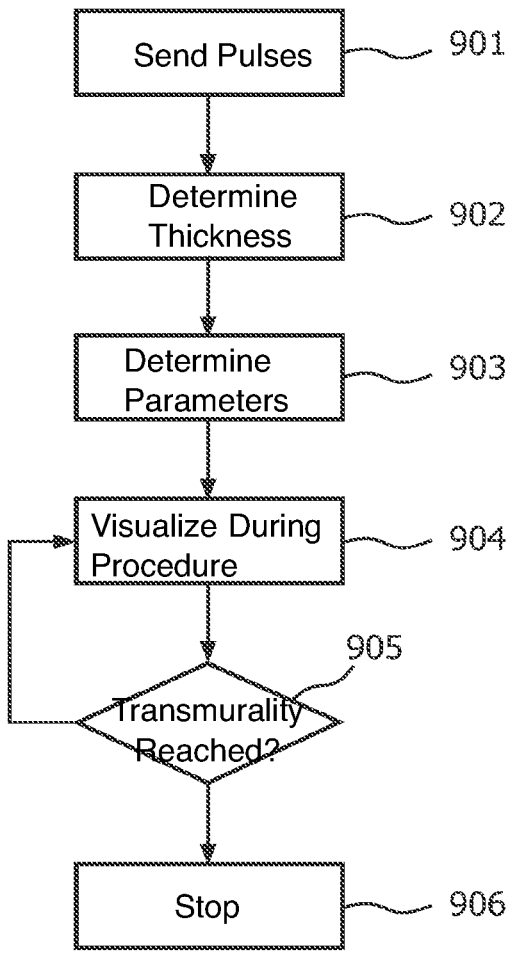
FIG. 27 shows exemplarily a further flowchart illustrating a monitoring method for monitoring an ablation procedure applied to an object.

A further embodiment of a monitoring method for monitoring an ablation procedure applied to an object is exemplarily described in the following with respect to a flowchart shown in FIG. 27.

A catheter tip comprising an ultrasound unit and an ablation element has been introduced into a heart of a human being or of an animal for ablating heart wall tissue. The position of the catheter tip has been determined. In step 901 the ultrasound unit sends ultrasound pulses out into the heart wall tissue, receives dynamic echo series after the ultrasound pulses have been reflected by the heart wall tissue, and generates the ultrasound signal depending on the received dynamic echo series.

In step 902, the ablation depth determination unit determines the thickness of the heart wall tissue at the position of the catheter tip, and in step 903 ablation parameters are determined based on the determined thickness of the heart wall tissue. This determination of the ablation parameters can be performed automatically, for example, by using predefined ablation parameters, which are stored in a storing unit and which are assigned to different heart wall tissue thicknesses and may be some further parameters influencing the selection of the ablation parameters, for example, the desired shape of the lesion, the location of the desired lesion within the heart, the age of the patient et cetera. Ablation parameters are, for example, the power and/or duration of the application of ablation energy. Furthermore, as an ablation parameter a degree of transmurality is defined by a user or automatically determined, for example, by using a look-up table stored in a storing unit.

In step 904, the ablation procedure starts and, while the heart wall tissue is ablated, the ultrasound unit produces ultrasound signals which are used by the ablation depth determination unit for determining the ablation depth and thickness of the heart wall tissue. Furthermore, in step 904 the ablation depth and the thickness of the heart wall tissue are visualized on the visualization unit. During the ablation procedure, the ablation depth determination unit calculates the degree of transmurality and checks in step 905 whether the degree of transmurality defined in step 903 has been reached. If this is the case, the ablation procedure and preferentially also the ultrasound monitoring stop in step 906. If the defined degree of transmurality has not been reached, the ablation procedure and the determination of the ablation depth and the thickness of the heart wall tissue continue.

The monitoring apparatus can comprise a beam former element for forming a beam defined by the ultrasound pulses. For example, a beam former element can be used in conjunction with a phased-array ultrasound system. Several of individually addressable transducer elements can be grouped into one "quasi-pixel". A possible advantage is the reduction in cables. Instead of, for example, 256 cables going to 256 transducers, only 16 cables going to 16 beam former elements may be used, wherein each of the beam former elements drives 16 transducers that are bonded onto them. In particular, directly (cable-less) bonded on them.

The monitoring apparatus is preferentially used in the minimally-invasive treatment of cardiac arrhythmias, wherein preferentially a radiofrequency (RF) ablation catheter comprising an ultrasound unit is used.

The monitoring apparatus allows actively controlling the ablation settings during treatment. Currently, the therapist relies on his own expertise to determine the optimal parameters for ablation, such as power, temperature, and duration. Note that these settings vary largely, due to sizable intra-patient differences of thickness of the local heart wall, perfusion, blood pressure and velocity, heart rhythm et cetera. Although a highly-skilled therapist is able to achieve successes with this approach, it is not always the case, and there are serious consequences for the patient when an error is made. The two major therapy-related problems result from either the under-heating or the overheating of the site. In the case of under-heating, the tissue is not sufficiently coagulated to form the arrhythmia-blocking lesion desired by the therapist. This can lead to persistent or recurring symptoms in the patient, and the requirement for subsequent treatment(s), longer periods of hospitalization, and greater risks of stroke and embolism. The other extreme, overheating, either causes rupturing of the tissue at the treatment site, releasing potentially life-threatening particles into the blood stream, or causes damage to neighboring organs and tissues. In the case that other organs are affected, fistulas can develop and these are often life-threatening (for example, a fistula in the esophagus has roughly a 75% mortality rate).

The monitoring apparatus in accordance with the invention provides a more adequate control of a RF catheter. The monitoring apparatus can provide feedback of the lesion development in the tissue, and can provide information about the depth of the lesion with respect to the thickness of the tissue at the treatment site. This allows preventing injuries and death from under-heating and overheating in RF catheter procedures.

Surgical ablation of atrial fibrillation (AF) is recommended for patients with persistent AF undergoing other cardiac surgical procedures. The advent of ablation technology has simplified the surgical treatment of AF, and completion of left atrial lesion sets requires generally only an additional 10 to 20 minutes operative time. This has increased the interest in ablating AF in patients presented for other surgical cardiac procedures. Note that these open-heart procedures involve generally cardiopulmonary bypass and are performed on a non-beating heart.

More recently, ablation technologies for thoracoscopic and keyhole approaches have become available allowing epicardial ablation of AF on a beating heart. This minimally invasive epicardial approach circumvents the need for cardiopulmonary bypass and total procedure times are two to four hours. However, these procedures do require the deflation of a lung, and as such are not trivial.

In the so-called Maze procedure, lesions are constructed to interrupt multiple, disorganized re-entrant currents that characterize AF. Such a procedure typically includes the isolation of the pulmonary veins combined with one or more other specific lesion sets. Such a specific lesion set 50 is schematically and exemplarily shown in FIG. 28.

Figure 28:
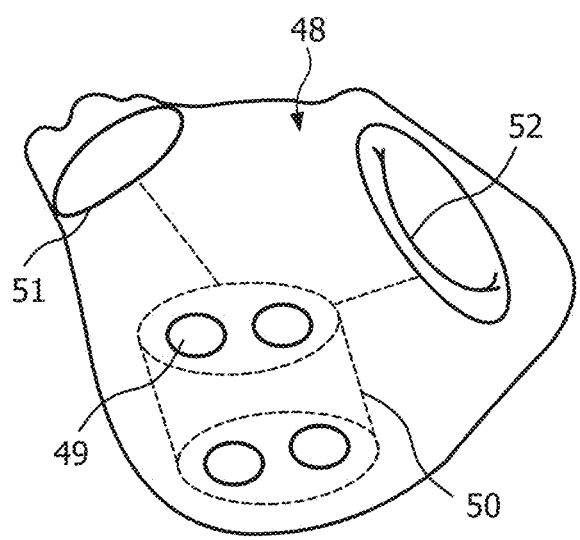
FIG. 28 shows schematically and exemplarily a lesion set in the heart.

FIG. 28 shows the left atrium 48 comprising the pulmonary veins 49. The schematic lesion set 50, including bilateral pulmonary veins isolation, is indicated in FIG. 28 by the dashed lines.

Line 52 indicates the mitral valve. Thus, a lesion line is drawn from the pulmonary vein openings 49 to the mitral valve. Furthermore, line 51 indicates the left arterial appendage. A lesion line is drawn from the pulmonary vein openings 49 to the left atrial appendage 51. In another embodiment, line 51 can indicate the septum. FIG. 28 shows a typical Maze procedure, which includes left atrial appendage exclusion and an isolation line stretching from the pulmonary vein openings encircling lines to a left atrial appendage exclusion.

For the minimal invasive (thoracoscopic) approach for epicardial ablation usually three different electrodes are used for ablation: 1) lasso electrode to create encircling lesion around pulmonary veins: 2) bipolar pen to "draw" ablation lines at the LA roof; 3) ablation pen for ablation of ganglionic plexi. The latter has integrated features for high frequency stimulation, pacing and sensing. Thus, the ablation systems described above with respect to FIGS. 18 to 25 are preferentially used for performing an epicardial ablation.

In general, during the ablation procedure cardiac tissue that is in contact with the energy source, i.e. with the ablation element like an ablation electrode, is exposed to high (~60° C.) or low (~50° C.) temperatures such that it is destroyed and a lesion of non-conducting scar tissue is formed. RF is preferentially used as energy source, whereas laser, HIFU, microwave and cryoablation comprise alternative techniques. The monitoring apparatus in accordance with the invention is preferentially used to monitor ablation procedures that either destroy pro-arrhythmogenic tissue sites or create a continuous and transmural line of block to prevent an electrical activation from crossing such a line of block.

The different technologies for epicardial ablations can be divided into those using unipolar energy sources and those that use a bipolar clamp. Bipolar RF ablation with a clamp can overcome some of the limitations of unipolar devices, including the difficulty of creating transmural lesions due to blood flow in the atrium. With a bipolar clamp, energy is delivered between two closely approximated electrodes embedded in the jaw of a clamp device resulting in the formation of discrete and transmural lesions. If an ablation of the right and LA isthmus is required, the additional use of unipolar ablation is preferentially used.

The monitoring apparatus is preferentially used for monitoring the minimally-invasive procedure of catheter ablation in the left atrium, used to block arrhythmogenic signals in the heart, especially for the treatment of atrial fibrillation.

In epicardial ablation procedures, the monitoring apparatus allows obtaining continuous and transmural lesions, even if this is difficult due to variations in atrial wall thickness and endocardial blood cooling. In addition, the monitoring apparatus allows providing the therapist with a direct indication that the lesion has become transmural. The assessment of transmurality has not to be based on indirect measures including impedance and electrical activity.

The monitoring apparatus can be used for surgical treatment of cardiac arrhythmias and uses ultrasound imaging for establishing the degree of lesion transmurality.

The monitoring apparatus allows determining the progression of the depth of the lesion during the ablation procedure, independent of the energy source used including RF and laser. The monitoring apparatus looks at dynamic changes of the ultrasound signal in time, since the signal changes most at a zone that corresponds to the tissue region where the treatment actively happens. The signal at each and every given time can be compared with the signal recorded at a previous time interval. So, the part of the ultrasound signal that changes most dramatically during ablation can be attributed to the boundary of the lesion which progresses through the tissue. In particular, the full time-resolved set of ultrasound data is stored in order to do the analysis and generally simply subtracting sequential data points (be the A-lines or 2D/3D images) will not result in meaningful information.

The monitoring apparatus can be adapted to perform a spatially one-dimensional imaging. For instance, the object being, for example, tissue is ablated for 60 seconds at 20 W using a manual unipolar RF catheter. Single A-lines (as shown in FIG. 2) are recorded with a sampling frequency of 20 Hz starting 10 seconds before the ablation and continued 20 seconds after ablation. The A-lines are filtered using a Hilbert filter and absolute amplitudes after filtering are converted into color intensity lines (brightness modulated), which are stitched together such that a two-dimensional graph is obtained. This two-dimensional graph represents the ultrasound signal that depends on the dynamic echo series of ultrasound pulses sent out into the object.

The invention can be used in tissue imaging during surgical treatment of cardiac arrhythmias. In these procedures it is desired to create transmural and continuous lesions in order to block electrical activity. In this invention a monitoring apparatus is proposed that uses ultrasound imaging for the direct visualization of the lesion in epicardial ablation. The monitoring apparatus allows using ultrasound imaging for real-time visualization of the progression of the lesion boundary.

This invention can be used in the field of catheter based cardiac ablation. This is especially relevant for catheter treatment of atrial fibrillation. There are at least three different applications for this invention: a) Measurement of heart wall thickness: Support for therapy planning where the ablation energy and duration is based on the measured heart wall thickness: b) Measurement of the lesion after ablation: The purpose is to verify lesion completeness and/or transmurality, when it is still possible for the electrophysiologists to easily go back to the incomplete lesion to add additional ablation points; c) Measurement of the created lesion during ablation. Here, the invention is used for treatment guidance, where the ablation is continued until the lesion measurement indicated that the lesion is continuous and/or transmural.

The invention can be used in tissue imaging during treatment of e.g. cardiac arrhythmias and tumor ablation. In these procedures it is desired to follow the progression of lesion formation during the procedure.

All arrangements located at a catheter tip disclosed above can be used with the monitoring apparatus in accordance with the invention, in particular, with the monitoring apparatus described above with reference to FIG. 10.

The monitoring apparatus can comprise any ultrasound unit that allows generating an ultrasound signal depending on received dynamic echo series after ultrasound pulses have been sent out to the object.

Although in the above described embodiments ablation elements are integrated together with an ultrasound unit in a catheter, these embodiments are preferred embodiments only and in another embodiment the monitoring apparatus can comprise a separate catheter including an ultrasound unit, wherein the ablation is performed by using another catheter.

Although in the above described embodiments certain configurations of ultrasound units, ablation elements and/or sensing elements are shown, the invention is not limited to a certain configuration of ultrasound units, ablation elements and/or sensing elements. In an embodiment, the monitoring apparatus does not comprise an ablation element and/or a sensing element. Furthermore, the monitoring apparatus does not even have to comprise an ultrasound unit. In an embodiment, the monitoring apparatus comprises an ultrasound signal providing unit being, for example, a storing unit in which the ultrasound signal is stored or an ultrasound signal receiving unit for receiving the ultrasound signal from an ultrasound unit.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of the ablation depth or of a heart wall thickness and/or ablation and/or sensing et cetera performed by one or several units or devices can be performed by any other number of units or devices. For example, the determination of the ablation depth or of the heart wall thickness can be performed by a single unit of by any other number of different units. The determinations and/or the control of the monitoring apparatus in accordance with the above described monitoring method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for planning an ablation procedure of an organ, comprising:
    a catheter comprising an ablation element and an ultrasound unit in its tip, wherein the system is configured for tracking a position of the catheter tip within the organ; and
    a computing system coupled to the catheter and configured to determine a thickness of a tissue wall of the organ from reflected ultrasound signals received by the ultrasound unit at the position of the catheter tip within the organ and wherein the computing system unit is configured to automatically determine an ablation parameter based on the determined thickness of the tissue wall, wherein the ablation parameter comprises a degree of transmurality, and to automatically discontinue the ablation procedure when the determined degree of transmurality exceeds a desired transmurality for the ablation procedure.

2. The system of claim 1, wherein the desired transmurality is a predetermined value based upon the position of a desired lesion within the patient.

3. The system of claim 2 wherein the computing system is further configured to store a look up table of parameters, wherein the desired degree of transmurality is determined based on the parameters in the look up table.

4. The system of claim 1, wherein the computing system is further-configured to store a plurality of predefined transmurality parameters, and wherein the ablation parameter is determined by comparing the determined transmurality to one of the predefined transmurality parameters.

5. The system of claim 4, wherein the predefined transmurality parameters are based on at least one of the position of a desired lesion within the organ, and/or an age of a patient.

6. The system of claim 1, wherein the computing system tracks the position of the catheter tip within the organ based on at least one of a:
   determination of the position and/or orientation of the catheter tip by using an X-ray fluoroscopy system;
   locating the catheter tip comprising a tracking coil by a magnetic resonance imaging system.

7. The system of claim 1, further comprising a visualization unit and wherein the system is configured to display the thickness of the tissue wall in an image of the organ at the position for which the respective thickness of the tissue wall has been determined.

8. The system of claim 7, wherein the thickness of the tissue wall is determined for multiple different locations within the organ.

9. The system of claim 1, further comprising an ablation unit connected to the ablation element, wherein the computing system is connected to the ablation unit and is configured to transmit the automatically determined ablation parameter to the ablation unit.

10. A method of planning an ablation procedure of an organ, comprising:
   tracking a position of a catheter tip within the organ;
   receiving reflected ultrasound signals by an ultrasound unit located in the tip of the catheter;
   determining a thickness of a tissue wall of the organ from the received ultrasound signals at the position of the catheter tip within the organ;
   determining an ablation parameter based on the determined thickness of the tissue wall, wherein the ablation parameter comprises a degree of transmurality; and
   automatically discontinuing ablation when the determined degree of transmurality exceeds a desired transmurality for the ablation procedure.

11. The method of claim 10, wherein the determining of the ablation parameter comprises selecting one of a plurality of predefined ablation parameters assigned to different tissue wall thicknesses.

12. The method of claim 11, wherein the predefined ablation parameters are based on the position of a desired lesion within the organ, and/or an age of a patient.

13. The method of claim 11, wherein the predefined ablation parameters are based on the position of a desired lesion within the organ, and/or an age of a patient.

14. The method of claim 10, wherein the method is performed by a computing system configured to determine the degree of transmurality is determined based on a look-up table stored by the computing system.

15. The method of claim 10 wherein the automatic discontinuing comprises obtaining the desired transmurality from a plurality of predetermined transmurality values stored in a lookup table of a computing system.

* * * * *